US011529271B2

(12) United States Patent
LaVon et al.

(10) Patent No.: US 11,529,271 B2
(45) Date of Patent: Dec. 20, 2022

(54) ABSORBENT ARTICLE WITH BELT HAVING ZONED ELASTICITY

(71) Applicant: The Procter & Gamble Company, Cincinnati, OH (US)

(72) Inventors: Gary D. LaVon, Liberty Township, OH (US); Koichi Morimoto, Beijing (CN); Chunmin Cheng, Beijing (CN); Ling Tong, Beijing (CN)

(73) Assignee: The Procter & Gamble Company, Cincinnati, OH (US)

(*) Notice: Subject to any disclaimer, the term of this patent is extended or adjusted under 35 U.S.C. 154(b) by 433 days.

(21) Appl. No.: 15/981,963

(22) Filed: May 17, 2018

(65) Prior Publication Data
US 2018/0333314 A1 Nov. 22, 2018

(30) Foreign Application Priority Data
May 18, 2017 (CN) ................ 2017/084808

(51) Int. Cl.
A61F 13/15 (2006.01)
A61F 13/64 (2006.01)
A61F 13/56 (2006.01)
A61F 13/49 (2006.01)
A61F 13/496 (2006.01)

(52) U.S. Cl.
CPC .......... A61F 13/64 (2013.01); A61F 13/4902 (2013.01); A61F 13/496 (2013.01); A61F 13/49011 (2013.01); A61F 13/565 (2013.01); A61F 2013/15146 (2013.01)

(58) Field of Classification Search
CPC ................ A61F 13/64; A61F 13/49011; A61F 13/4902; A61F 13/565; A61F 2013/15146; A61F 2013/49025
USPC ............ 604/385.24, 385.26, 385.27, 385.28, 604/385.29, 385.3
See application file for complete search history.

(56) References Cited

U.S. PATENT DOCUMENTS

| 7,955,311 | B2 | 6/2011 | Tanaka et al. |
| 8,133,212 | B2 | 3/2012 | Takada et al. |
| 8,518,009 | B2 | 8/2013 | Saito et al. |
| 9,107,777 | B2 | 8/2015 | Kinoshita et al. |
| 9,827,149 | B2 | 11/2017 | LaVon et al. |
| 2005/0107763 | A1 | 5/2005 | Matsuda et al. |
| 2008/0195072 | A1 | 8/2008 | Warner |

(Continued)

FOREIGN PATENT DOCUMENTS

| CN | 101541284 A | 9/2009 |
| CN | 102088943 A | 6/2011 |

(Continued)

OTHER PUBLICATIONS

International Search Report and Written Opinion, PCT/CN2017/084808, dated Feb. 12, 2018.

(Continued)

Primary Examiner — Jacqueline F Stephens
(74) Attorney, Agent, or Firm — Charles R. Matson; Richard L. Alexander

(57) ABSTRACT

The disclosure relates to absorbent articles having at least a first belt which comprises a first, second and third zone. The at least first belt provides improved fit in the low motion zone of a wearer while being able to adapt easily to the motion of the wearer outside the low motion zone.

15 Claims, 11 Drawing Sheets

(56) References Cited

U.S. PATENT DOCUMENTS

| | | |
|---|---|---|
| 2012/0330263 A1 | 12/2012 | Lawson |
| 2013/0079742 A1 | 3/2013 | Kuwano et al. |
| 2013/0079743 A1 | 3/2013 | Mukai et al. |
| 2013/0123736 A1 | 5/2013 | Ichikawa |
| 2013/0138072 A1 | 5/2013 | Morimoto |
| 2013/0211363 A1 | 8/2013 | Lavon |
| 2013/0261589 A1* | 10/2013 | Fujkawa ............ A61F 13/49012 604/385.29 |
| 2013/0274700 A1 | 10/2013 | Harris |
| 2013/0310785 A1 | 11/2013 | Wade et al. |
| 2015/0320611 A1 | 11/2015 | Seitz et al. |
| 2015/0359685 A1 | 12/2015 | Lavon et al. |
| 2016/0058627 A1 | 3/2016 | Barnes et al. |
| 2016/0184145 A1 | 6/2016 | Morimoto |
| 2017/0049637 A1 | 2/2017 | Mori |
| 2017/0165129 A1 | 6/2017 | Morimoto et al. |
| 2017/0281417 A1 | 10/2017 | Ishikawa |
| 2018/0333313 A1 | 11/2018 | Lavon et al. |

FOREIGN PATENT DOCUMENTS

| | | |
|---|---|---|
| CN | 203001261 U | 6/2013 |
| CN | 203677383 U | 7/2014 |
| CN | 203852490 U | 10/2014 |
| CN | 204290984 U | 4/2015 |
| CN | 204909840 U | 12/2015 |
| CN | 204951357 | 1/2016 |
| CN | 106038086 A | 10/2016 |
| JP | 2012148069 A | 8/2012 |
| JP | 2013116196 A | 6/2013 |
| JP | 2015142685 A | 8/2015 |
| JP | 2016198219 | 12/2016 |
| WO | 2012090931 A1 | 7/2012 |
| WO | 2016098532 A1 | 6/2016 |
| WO | 2016101198 A1 | 6/2016 |
| WO | 2016203602 A1 | 12/2016 |
| WO | 2017070142 A1 | 4/2017 |
| WO | 2018209631 A1 | 11/2018 |

OTHER PUBLICATIONS

International Search Report and Written Opinion, PCT/CN2017/084808.
All Office Actions, U.S. Appl. No. 15/981,959.
All Office Actions; U.S. Appl. No. 17/872,080, filed Jul. 25, 2022.
Unpublished U.S. Appl. No. 17/872,080, filed Jul. 25, 2022, to Gary Dean LaVon et al.

* cited by examiner

ABSORBENT ARTICLE WITH BELT HAVING ZONED ELASTICITY

CROSS REFERENCE TO RELATED APPLICATION

This application claims priority under 35 U.S.C. § 119 to Chinese Patent Application Serial No. CN2017/084808, filed on May 18, 2017, the entire disclosure of which is hereby incorporated by reference.

FIELD

This disclosure relates to absorbent articles providing sustained dynamic fit about the wearer. The absorbent article comprises at least a first belt. The first belt comprises elastic strands extending along a transverse direction and being disposed between a first and second belt layer. The elastic strands are provided as first, second and third plurality of elastic strands disposed in a first, second and third zone of the first belt.

BACKGROUND

Infants and other incontinent individuals wear absorbent articles to absorb and contain urine and other body exudates. Absorbent articles function both to contain the discharged materials and to isolate these materials from the body of the wearer and from the wearer's garments and bed clothing.

However, absorbent articles have a tendency to sag or gap away from and to slide/slip down on the body of the wearer during use. This sagging/gapping and sliding/slipping is caused by the relative motions of the wearer as the wearer breathes, moves and changes position, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer.

Conventional absorbent articles are typically designed to fit high on the abdomen of the wearer and down on the thighs such that the article fits in the zones of the wearer that are subject to dynamic motion (and thus dynamic forces) during use. These dynamic motions and forces, especially by the abdomen bulging and contracting, tend to deform the materials making up the article and tend to push the article away from the body. Thus, the article tends to sag/gap away from the body. The anchoring system of prior art articles is also typically designed to form a defined dimension of the waist and leg openings and a horizontal line of tension (imparts a tensile force along a line) about the wearer to secure the diaper on the wearer. However, the horizontal line of tension created by prior art articles cannot accommodate the changes in body dimension caused by wearer movement such that the diaper tends to slide/slip down on the wearer when the dimension of the abdomen of the wearer changes. The prior art articles slide/slip down the abdomen setting below the belt at an area of smaller dimension which leads to gapping at the waist and legs. Further, the absorbent core and other stiff non-elastic elements of prior art articles disposed in the zones of the abdomen or legs that undergo such dynamic forces are pushed downward or inward by the dynamic forces resulting in further gapping/sliding of the product on the wearer.

Absorbent articles are commonly available in taped and pant type articles, as well as inserts. Typically, taped articles are packaged without being pre-closed, whereas pant articles are pre-closed. Pant articles are often used for potty training, but not necessarily. Generally, pants tend to have higher forces just above the leg opening and at the waist to anchor the article to the wearer. These areas are, however, zones, where the anatomy of the wearer moves a lot as the wearer moves. Relatively High forces in these "high motion zone" thus tend to result in red marking of the skin and restriction of freedom of movement.

Thus, it would be advantageous to provide an absorbent article that provides better fit, reduced leakage, and wearer comfort. It would further be advantageous to provide an absorbent article which has reduced sagging and gapping as well as reduced overall sliding/slipping of the absorbent article on the wearer during use.

SUMMARY OF THE INVENTION

The disclosure relates to an absorbent article comprising a longitudinal and transverse dimension. The absorbent article comprises front waist region with a front waist edge and a rear waist region with a rear waist edge, and a crotch region extending between the front and rear waist region. The absorbent article comprises a center chassis and a first belt.

The center chassis comprises a first transverse edge, a second transverse edge, a first longitudinal side edge and a second longitudinal side edge, a liquid permeable topsheet, a liquid impermeable backsheet and an absorbent core disposed between the topsheet and the backsheet.

The first belt comprises a first belt layer disposed on an interior surface of the first belt, a second belt layer disposed on an exterior surface of the first belt and elastic stands extending substantially along the transverse direction disposed between the first belt layer and the second belt layer.

The first belt comprises a first zone, a second zone and a third zone; the first zone being provided adjacent to the rear waist edge, and the second zone being provided between the first and third zone in transverse direction of the absorbent article.

The elastic strands of the first zone comprise a first plurality of elastic stands which are attached to one or both of the first belt layer and the second belt layer at or adjacent the transversally opposing ends of the elastics of the first plurality of elastic strands. The elastic strands of the first plurality of elastic strands are not attached to one or both of the first belt layer and second belt layer along substantially the complete length of the elastic strands.

The first belt layer and second belt layer are joined to each other between pairs of elastic strands of the first plurality of elastic strands in the first zone.

The elastic strands of the second zone comprise a second plurality of elastic strands that are attached to one or both of the first belt layer and second belt layer along substantially the complete length of the elastic strands.

The elastic strands of the third zone comprise a third plurality of elastic strands which are attached to one or both of the first belt layer and the second belt layer at or adjacent the transversally opposing ends of the third plurality of elastic strands. The elastic strands of the third plurality of elastic strands are not attached to one or both of the first belt layer and second belt layer along substantially the complete length of the elastic strands.

The first belt layer and second belt layer are joined to each other between pairs of elastic strands of the third plurality of elastic strands in the third zone.

The first belt of the absorbent article may comprise elastic strands which are severed and the number of non-severed elastic strands extending substantially across the complete transverse dimension in the first belt may higher than the number elastic strands which were severed.

The absorbent article may further comprise a second belt. The second belt of the absorbent article may comprise elastic strands which are severed and the number of non-severed elastic strands extending substantially across the complete transverse dimension in the second belt may lower than the number elastic strands which were severed.

The absorbent article of any of the preceding claims, wherein neighboring elastic strands of all pluralities of elastic strands in the first and the optional second belt may be spaced apart from each other in the longitudinal direction of the absorbent article by a gap of from 2 to 15 mm.

The first and second belt layer and the optional third and fourth belt layer may comprise apertures.

DETAILED DESCRIPTION

Figure 1:
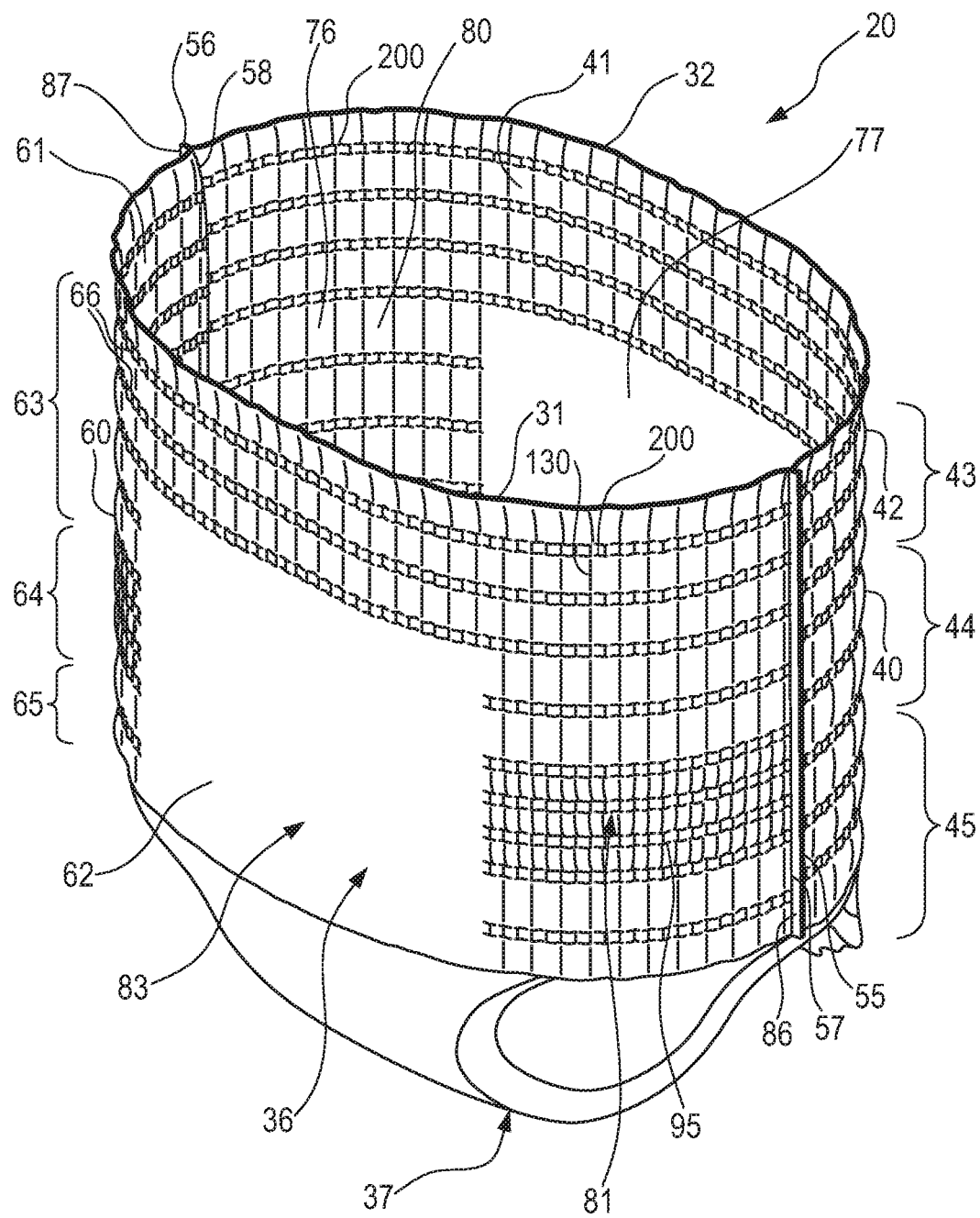
FIG. 1 is a perspective view of an exemplary absorbent article of the present disclosure with permanent side seams, disposed as it would be around a wearer.
Figure 2:
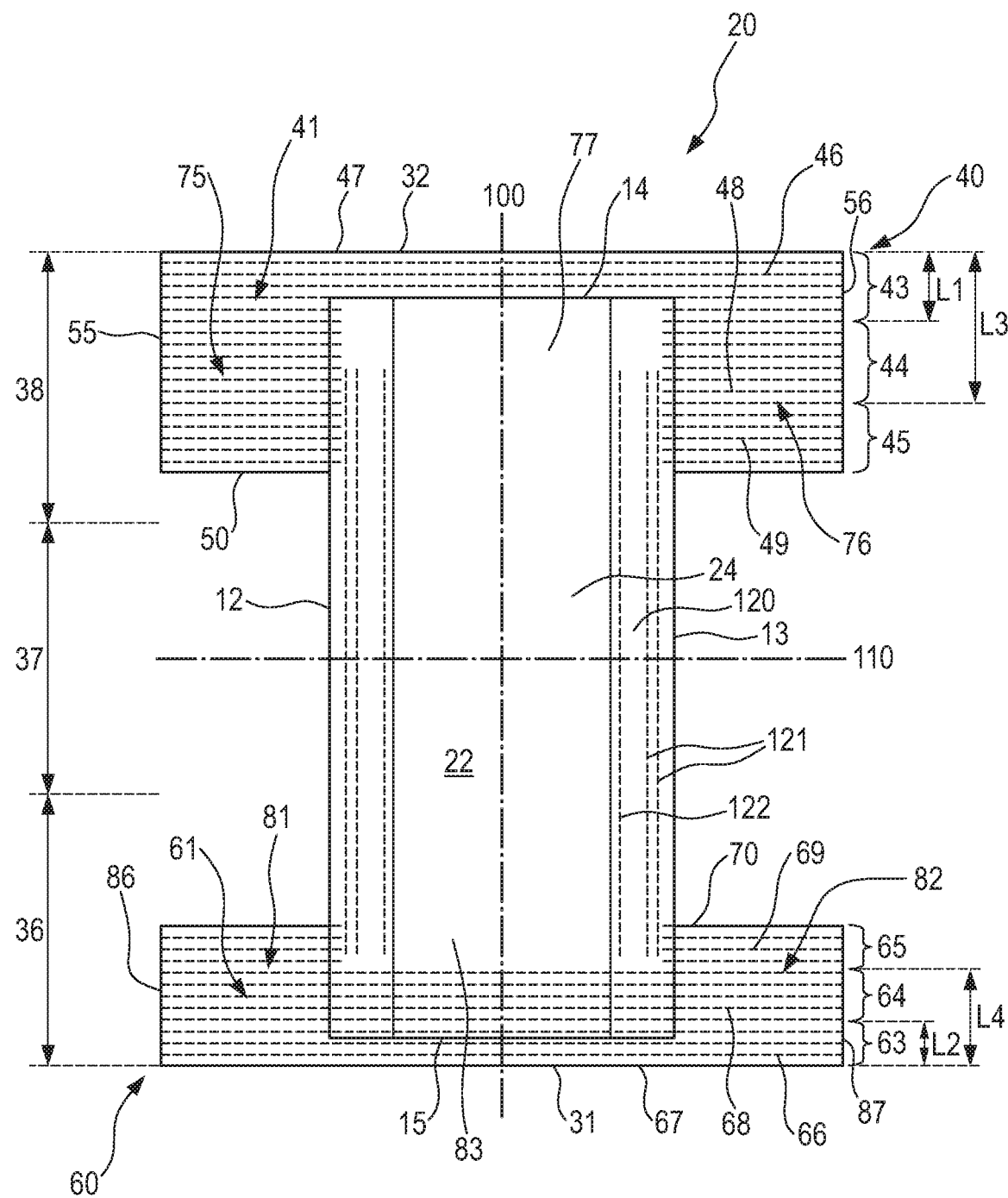
FIG. 2 is a plan view of an exemplary absorbent article of the present disclosure, laid out flat.

As used herein, the following terms shall have the meaning specified thereafter:

As used herein, "absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants (for babies or for adults), absorbent inserts (which are intended to be inserted into an outer cover to form a diaper or pant), feminine care absorbent articles such as sanitary napkins or pantiliners, and the like. As used herein, the term "exudates" includes, but is not limited to, urine, blood, vaginal discharges, sweat and fecal matter. Preferred absorbent articles of the present disclosure are disposable absorbent articles, more preferably disposable diapers and disposable pants.

As used herein, "disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wet wipe for personal hygiene use, the disposable absorbent article is most often intended to be disposed after single use.

"Non-extensible" as used herein refers to a material which, upon application of a force, elongates beyond its original length by less than 30% if subjected to the following test: A rectangular piece of the material having a width of 2.54 cm and a length of 25.4 cm is maintained in a vertical position by holding the piece along its upper 2.54 cm wide edge along its complete width. A force of 10 N is applied onto the opposite lower edge along the complete width of the material for 1 minute (at 25° C. and 50% rel. humidity; samples should be preconditioned at these temperature and humidity conditions for 2 hours prior to testing). Immediately after one minute, the length of the piece is measured while the force is still applied and the degree of elongation is calculated by subtracting the initial length (25.4 cm) from the length measured after one minute.

If a material elongates beyond its original length by more than 30% if subjected to the above described test, it is "extensible" as used herein.

"Highly non-extensible" as used herein refers to a material, which, upon application of a force, elongates beyond its original length by less than 15% if subjected to the test described above for "non-extensible" material.

"Non-elastic" as used herein refers to a material which does not recover by more than 20% if subjected to the following test, which is to be carried out immediately subsequent to the test on "non-extensibility" set out above.

Immediately after the length of the rectangular piece of material has been measured while the 10N force is still applied, the force is removed and the piece is laid down flat on a table for 5 minutes (at 25° C. and 50% rel. humidity) to be able to recover. Immediately after 5 minutes, the length of the piece is measured again and the degree of elongation is calculated by subtracting the initial length (25.4 cm) from the length after 5 minutes.

The elongation after one minute while the force has been applied (as measured with respect to "non-extensibility") is compared to the elongation after the piece has been laid down flat on a table for 5 minutes: If the elongation does not recover by more than 20%, the material is considered to be "non-elastic".

If a material recovers by more than 20%, the material is considered "elastic" as used herein.

"Highly non-elastic" as used herein refers to a material, which is either "non-extensible" or which does not recover by more than 10% if subjected to the test set out above for "non-elastic".

For use as first, second, third or fourth belt layers of the present disclosure, extensible, non-extensible, highly non-extensible, elastic, non-elastic and highly non-elastic relate to the dimension of the material, which, once the material has been incorporated into the structure, is parallel to the transverse centerline of the absorbent article. Hence, the sample length of 25.4 cm for carrying out the tests described above corresponds to the transverse direction of the first, second, third and fourth belt layer once the belt layer has been incorporated into the absorbent article.

As used herein, the term "comprises" is an open ended term which means that other features, components, items or steps can be added. The term "comprises" as used herein includes the terms "essentially consisting of" and "consist of". "Consist of" denotes that only the features, components or steps following the term "consist of" are included with no further features, components, items or steps.

As used herein, "diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

"Longitudinal" means a direction running substantially perpendicular from a waist edge to a longitudinally opposing waist edge of an absorbent article when the article is in a flat out, uncontracted state.

"Transverse" refers to a direction running from a longitudinally extending side edge to a transversally opposing longitudinally extending side edge of an article and generally at a right angle to the longitudinal direction.

"Proximal" and "Distal" refer respectively to the location of an element relatively near to or far from the longitudinal or transversal centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

Absorbent Article

Figure 8:
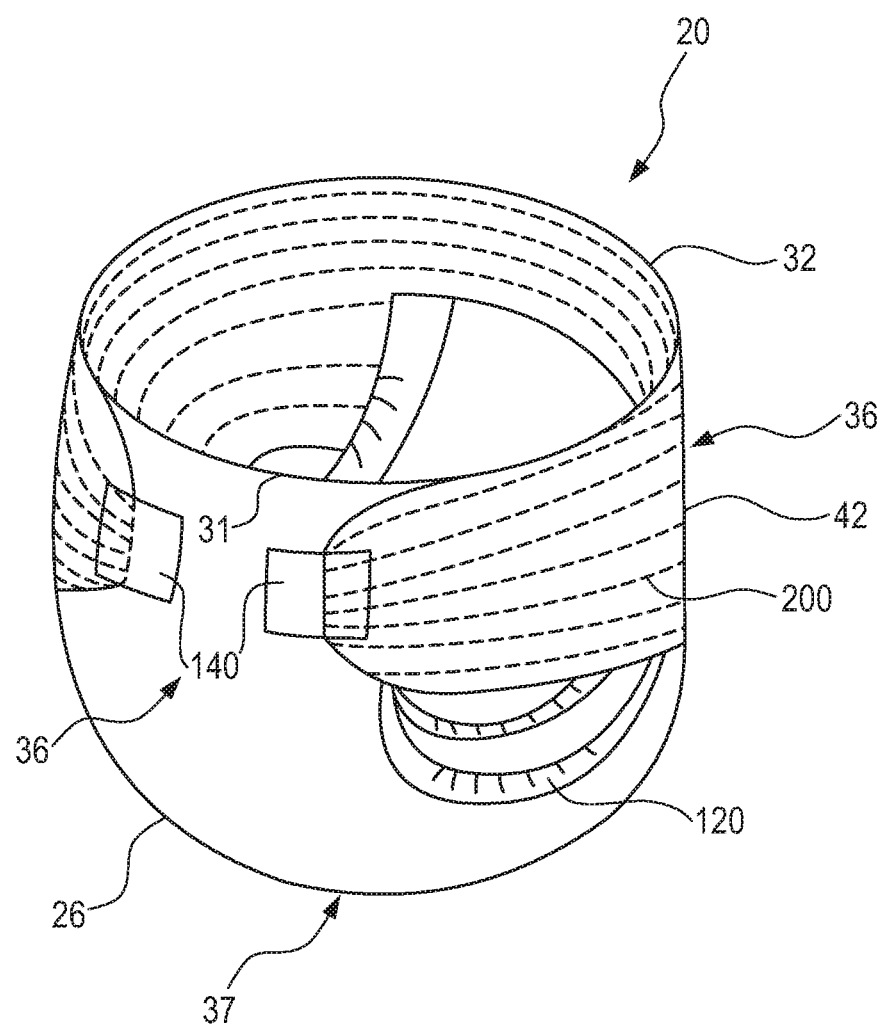
FIG. 8 is a perspective view of the absorbent article shown in FIG. 6 in a fastened configuration, disposed as it would be around a wearer.

An absorbent article 20 as disclosed herein is exemplarily shown in FIGS. 1, 2, 4, 5, 7 and 8, with FIGS. 2, 4, 5 and 7 being plan views of the absorbent articles laid out flat and the body-facing surface facing towards the viewer; and FIGS. 1 and 8 being perspective views of the absorbent articles, disposed as it would be around a wearer. The absorbent article 20 has a longitudinal centerline 100 with a longitudinal dimension and a transverse centerline 110 with a transverse dimension. The article 20 has a front waist region 36 with a front waist edge 31 and a rear waist region 36 with a rear waist edge 32. A crotch region 37 is disposed between and connecting the front and rear waist region. The front and rear waist edges 31 and 32 together form a waist opening to encircle the waist of the wearer when the article is applied on a wearer. When the absorbent article 20 is applied on a wearer, the absorbent article further comprises a pair of leg openings to encircle the legs of the wearer. If the absorbent article is a pant, the waist opening and the pair of leg openings will already be pre-formed before the absorbent article is applied on a wearer.

The absorbent article 20 comprises a center chassis 22. The center chassis comprises a liquid impermeable backsheet 26, a liquid permeable topsheet 24, and an absorbent core (not shown in the Figures) disposed between the backsheet and topsheet. The center chassis 22 has a first transverse edge 14 and a second transverse edge 15, a first longitudinal side edge 12 and a second longitudinal side edge 13. The first transverse edge 14 is disposed in the rear waist region 38 and the second transverse edge 15 is disposed in the front waist region 36.

The absorbent article 20 further comprises a first belt 40 and may optionally comprise a second belt 60. The first belt 40 and the optional second belt 60 may each comprise first and second longitudinal belt side edges 55 and 56, respectively, and each comprise first and second transverse belt side edges. The first belt 40 may be disposed in the rear waist region 38 such that the rear waist edge 32 of the absorbent article 20 is formed by the first transverse belt side edge of the first belt 40.

If the absorbent article 20 comprises a second belt 60, the second belt 60 may be disposed in the front waist region 36 such that the front waist edge 31 of the absorbent article 20 is formed by the first transverse edge of the second belt 60.

The center chassis 22 may be attached to the first belt 40, for example by joining the center chassis at or adjacent to its first transverse edge 14 to the first belt 40. If the absorbent article 20 comprises a second belt 60, the center chassis 22 may also be attached to the second belt 60, for example by joining the center chassis at or adjacent to its second transverse edge 15 to the second belt 60. The center chassis 22 may be attached to the first belt 40 and the optional second belt 60 by any means known in the art, such as by adhesive, ultrasonic bonding, pressure bonding, thermal bonding, or combinations thereof.

The center chassis 22 extends through the crotch region 37 of the absorbent article and may extend into the front and rear waist region 36 and 38. The longitudinal dimension of the center chassis 22 may be the same as the longitudinal dimension of the absorbent article. The first transverse edge 14 of the center chassis 22 may coincide with the rear waist edge 32 of the absorbent article 20 and the second transverse edge 15 of the center chassis 22 may coincide with the front waist edge 31 of the absorbent article 20. Alternatively, and preferably, the center chassis 22 may have a longitudinal dimension which is shorter than the longitudinal dimension of the absorbent article 20, such that the first transverse edge 14 of the center chassis 22 is transversely offset from the rear waist edge 32 of the absorbent article 20 and the second transverse edge 15 of the center chassis 22 is transversely offset from the front waist edge 31 of the absorbent article 20. In still another alternative, the center chassis 22 may have a longitudinal dimension shorter than the longitudinal dimension of the absorbent article 20, such that the first transverse edge 14 of the center chassis 22 is transversely offset from the rear waist edge 32 of the absorbent article 20 while the second transverse edge 15 of the center chassis 22 coincides with the front waist edge 31 of the absorbent article 20. In yet another alternative, the center chassis 22 may have a longitudinal dimension shorter than the longitudinal dimension of the absorbent article 20, such that the first transverse edge 14 of the center chassis 22 coincides with the rear waist edge 32 of the absorbent article 20 and the second transverse edge 15 of the center chassis 22 is transversely offset from the front waist edge 31 of the absorbent article 20 (in this embodiment, the absorbent article would comprise a second belt).

However, if the absorbent article does not comprise a second belt 60, the second transverse edge 15 of the center chassis 22 may form a portion or all of the front waist edge 31 of the absorbent article 20. For such absorbent articles 20, the first transverse edge 14 of the center chassis 22 may or may not be transversely offset from the rear waist edge 32 of the absorbent article (it is, however, desirable that it is transversely offset from the rear waist edge).

Generally, if the center chassis 22 is transversely offset from the front and/or rear waist edge 31/32, the offset in the front and/or rear waist edge 31, 32 may be from 3 to 30% of the overall longitudinal dimension of the absorbent article 20, or from 5 to 25% of the overall longitudinal dimension of the absorbent article.

In preferred embodiments, the center chassis 22 is longitudinally offset from the front waist edge 31 of the absorbent article 20 less than it is offset from the rear waist edge 32 of the absorbent article 20. The ratio of the rear offset to the front offset may be from 1.1 to 5, preferably from 1.5 to 3. The offset ensures that the center chassis 22 resides predominantly within the low motion zone of the wearer (see below for more details). This is critical as the center chassis may be made of non-extensible or highly non-extensible materials. (Notably here, in deviation from the test methods set out above, for the use of the term "non-extensible" and highly non-extensible" in relation to the center chassis, the direction of extensibility is determined in the longitudinal direction. Hence, the sample length of 25.4 cm for carrying out the tests described above corresponds to the longitudinal direction of the materials as they then get incorporated into the center chassis.)

FIGS. 2, 4, 5 and 7 are plan views of an exemplary, non-limiting embodiment of absorbent articles 20 of the present disclosure in a flat, uncontracted state (i.e., without elastic induced contraction). The body-facing surface of the absorbent article 20 is facing the viewer. The absorbent article 20 includes a longitudinal centerline 100 and a transverse centerline 110. The absorbent article 20 comprises a center chassis 22, a first belt 40 and a second belt 60. The second belt may be provided in the front waist region 36 and is optional. The absorbent article 20 is shown to have a front waist region 36, a rear (or back) waist region 38 opposed to the front waist region 36, and a crotch region 37 located between the front waist region 36 and the rear waist region 38. The waist regions 36 and 38 generally comprise those portions of the absorbent article 20 which, when worn, encircle the waist of the wearer. The waist regions 36 and 38 include elastic strands 200 such that they gather about the waist of the wearer to provide improved fit and containment. The crotch region 37 is that portion of the absorbent article 20 which, when the absorbent article 20 is worn, is generally positioned between the legs of the wearer.

Center Chassis

The absorbent article 20 comprises a center chassis 22. The center chassis 22 comprises a liquid impermeable backsheet 26, a liquid permeable topsheet 24, and an absorbent core disposed between the backsheet and topsheet. The center chassis 22 has a first transverse edge 14 and second transverse edge 15, a first longitudinal side edge 12 and a second longitudinal side edge 13. The first transverse edge 14 is disposed in the rear waist region 38 and the second transverse edge 15 is disposed in the front waist region 36.

The center chassis 22 has opposing first and second longitudinal side edges 12 and 13 that may be oriented generally parallel to the longitudinal centerline 100. However, for better fit, first and second longitudinal side edges 12 and 13 may be curved or angled to produce, for example, an "hourglass" shaped absorbent article when viewed in a plan view. The center chassis 22 has opposing first and second transverse edges 14 and 15 that may be straight and oriented generally parallel to the transverse centerline 110.

The center chassis 22 comprises a liquid permeable topsheet 24, a liquid impermeable backsheet 26, and an absorbent core between the topsheet 24 and the backsheet 26. The absorbent core has a body-facing surface and a garment-facing-surface. The topsheet 24 may be joined to the absorbent core and/or the backsheet 26. The backsheet 26 may be joined to the absorbent core and/or the topsheet 24. The center chassis may have other structures, elements, or substrates which may be positioned between the absorbent core and the topsheet 24 and/or backsheet 26, such as a fluid acquisition system disposed between the absorbent core and the topsheet 24. The center chassis 22 may comprise additional features. While the topsheet 24, the backsheet 26, and the absorbent core may be assembled in a variety of well-known configurations, suitable configurations are described generally in U.S. Pat. Nos. 3,860,003; 5,151,092; 5,221,274; 5,554,145; 5,569,234; 5,580,411; and 6,004,306.

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U.

Any portion of the topsheet 24 may be coated with a lotion or skin care composition as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the absorbent core 28. Suitable structures including elasticized or foreshortened topsheets are described in more detail in U.S. Pat. Nos. 4,892,536; 4,990,147; 5,037,416; and 5,269,775.

The absorbent core may comprise a wide variety of liquid-absorbent materials commonly used in disposable diapers, pants and other absorbent articles. Examples of suitable absorbent materials include comminuted wood pulp, which is generally referred to as air felt, creped cellulose wadding, melt blown polymers, including co-form; chemically stiffened, modified or cross-linked cellulosic fibers; tissue, including tissue wraps and tissue laminates; absorbent foams; absorbent sponges; superabsorbent polymers (SAPs); or any other known absorbent material or combinations of materials. The absorbent materials may be contained by one or more core wrap layers, which may include a core cover (top layer facing towards the body) and a dusting layer (bottom layer facing towards the garment). The core wrap layers may be nonwoven webs. At least a portion, or all of, the absorbent core may be substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of SAP in particulate form in the absorbent core may vary, and may be greater than about 80% by weight of the absorbent core, or greater than about 85% by weight of the absorbent core, or greater than about 90% by weight of the absorbent core, or greater than about 95% by weight of the core (the core wrap layers, if present, are excluded when calculating the percentage). The absorbent core may comprise adhesive for example to help immobilizing the SAP within the core wrap layers and/or to ensure integrity of the core wrap layers.

Exemplary absorbent structures for use as the absorbent core are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The liquid impermeable backsheet 26 is generally positioned such that it may form at least a portion of the garment-facing surface of the absorbent article 20. Backsheet 26 may be designed to prevent the exudates absorbed by and contained within the absorbent article 20 from soiling articles that may contact the absorbent article 20, such as bed sheets and undergarments. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. A suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover layer and an inner layer. The outer cover layer may be made of a non-woven material. The inner layer may be made of a film. The backsheet 26 may comprise a graphic patch layer. At least one of the layers may comprise a single color or multi-color prints on one or more of the surfaces. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR.

The absorbent article 20 may include a leg gasketing system 120. The leg gasketing system 70 may comprise an inner leg cuff comprising an inner cuff folded edge and an inner cuff material edge. The leg gasketing system 120 may further comprise an outer cuff comprising an outer cuff folded edge and an outer cuff material edge. The leg gasketing system 120 may be a component of the center chassis.

The leg gasketing system 120 may comprise only the inner leg cuff.

The inner and outer leg cuffs may be formed by films and/or nonwovens and may be joined using adhesives. In one embodiment, the leg gasketing system 120 comprises one web of material. In another embodiment, at least part of the leg gasketing system 120 may be formed with a separate web material, a part of the topsheet 24 and/or part of the backsheet 26.

The outer leg cuff may comprise elastic members 121 positioned in a transversal array between the outer cuff folded edge and outer cuff material edge; the outer leg cuff optionally comprises at least two elastic members, or at least three elastic member, but may comprise not more than five elastic members. In one embodiment, the elastic members may be disposed between the outer cuff folded edge and the inner cuff material edge.

The leg gasketing system 120 may have an inner leg cuff comprised of an inner cuff folded edge and an inner cuff material edge, and between one and four elastic members 122. The leg gasketing system 120 may further comprise an outer cuff comprising an outer cuff folded edge and an outer cuff material edge.

Low Motion Zone

Figure 9C:
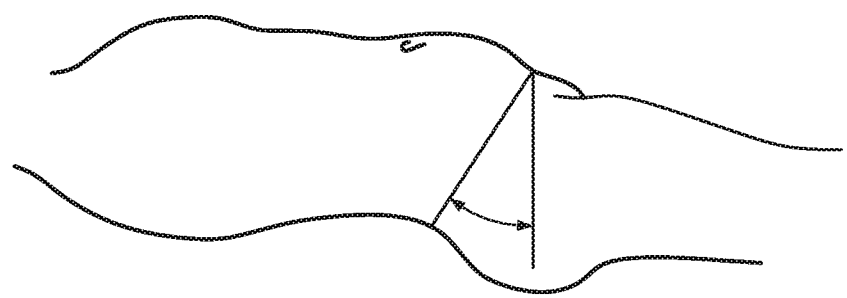
FIG. 9C is a side view of the body of a wearer showing the angle of the primary line of tension which can be created by an absorbent article of the present disclosure.
Figure 9B:
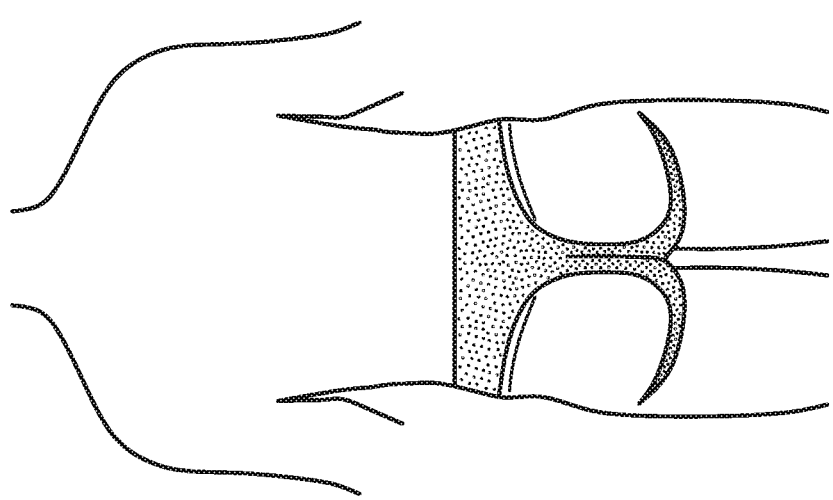
FIG. 9B is a back coronal view of the body of a wearer showing certain anatomical features and the location of the low motion zone.
Figure 9A:
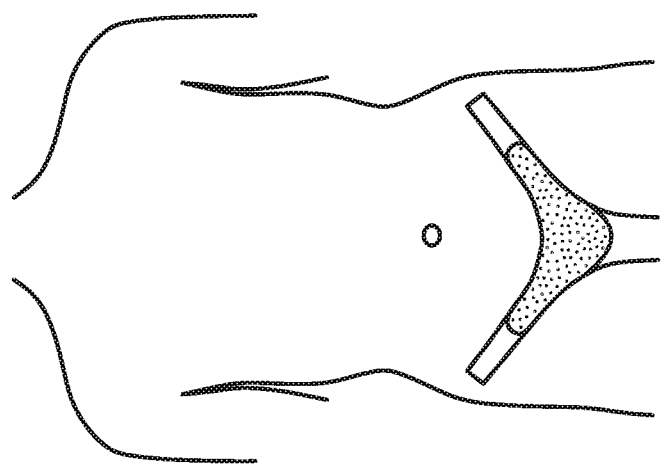
FIG. 9A is a front coronal view of the body of a wearer showing certain anatomical features and the location of the low motion zone.

FIGS. 9A and 9B show front and rear views of a wearer showing where the low motion zone of the wearer is located. The shaded zones in the drawings delineate the low motion zone. As defined by the anatomy of the wearer, the "low motion zone" is defined to mean the zone or area of the body, which despite dynamic movements remains substantially undeformed or undergoes very little motion. As shown in FIG. 9A, the low motion zone is bounded by the arcuate line in the hypo gastric abdominal region connecting each anterior superior iliac spine, "S", through the crease or fold created by the rectus abdominus muscle, hereinafter the abdominal crease, "T". The abdominal crease is typically the fold or flexion crease of skin or muscle created by the abdomen when the wearer goes into a sitting position. The low motion zone is bounded on each transversal side by an arcuate line connecting the anterior superior iliac spine through the perineum along the inguinal ligament under the gluteus maximus (along the gluteal fold) to about the posterior inferior iliac spine, hereinafter the leg crease, "L". As shown in FIG. 9B, the low motion zone is bounded on the posterior of the wearer by the line connecting the posterior inferior iliac spine over the gluteous maximus and along the lumbar curve of the back, "R" (the small of the back). For purposes of the present disclosure, the low motion zone also includes the zone or area of the gluteous maximus (although not shaded in FIG. 9B) despite the fact that the gluteous maximus undergoes some dynamic motion since the forces generated in this zone caused by the wearer's movements tend to push the article upward over the buttocks into the lumbar curve to enhance the fit of the article rather than degrade such fit.

The first belt and the optional second belt of the absorbent article of the present disclosure can provide the article with an "anchoring system" for anchoring the article about the wearer throughout the absorbent article's use so the absorbent article has a reduced likelihood to sag/gap and slide/slip during use. The anchoring system provides a line or lines (zone) of tension (hereinafter, the primary line of tension) substantially about the perimeter of the low motion zone that imparts anchoring forces to maintain the position of the absorbent article throughout wearing. As shown in FIG. 9C, the primary line of tension is disposed at an angle, a, to the horizontal on the body of the wearer (an angle to the transverse direction of the absorbent article) such that the primary line of tension extends from around the lumbar curve of the back (the "small of the back") over the iliac crest of the hips to the abdominal crease. Thus, the primary line of tension is disposed in the zone of minimal changing body dimension (i.e., the primary line of tension is not disposed over the abdomen or the gluteous maximus which increase and decrease in dimension during movement), such that the primary line of tension stabilizes and maintains anchoring forces which maintain the position of the absorbent article on the wearer such that the absorbent article is unlikely to slide or slip downward during use due to the movements of the wearer or to the force of the increased weight of the absorbent article when it is loaded. The angled primary line of tension created by the anchoring system also imparts an upward anchoring force on the absorbent article tending to pull the absorbent article up on the body, and thus counteract the weight force of the loaded article, since the primary line of tension has a vector component in the longitudinal direction. The normal anchoring forces created by the primary line of tension (another vector component of the angled primary line of tension) anchor the absorbent article in the low motion zone since the normal anchoring forces act compressively to bring the article and body into intimate contact. These normal anchoring forces thus assist in maintaining the fit of the absorbent article as well as reducing leakage since the article and especially the absorbent core is maintained in a substantially fixed position and in close relationship with the body. The angled primary line of tension also tends to reduce red-marking of the skin, since the anchoring forces are disposed in the low motion zone such that the body dimension is not increasing or decreasing along the primary line of tension which could cause red marking.

The belt(s) of the absorbent article of the present disclosure can place higher stress in the low motion zone, between the leg opening area and the waist opening area compared to the areas of the belt which are outside the low motion zone. In the first and second belt, the second and the optional fifth zones are the areas which can apply higher stress compared to the first, third and optional fourth and sixth zone due to the way the elastic strands are applied to the belt. This is explained in more detail below. Thereby, an absorbent article is provided with sustained within the perimeter of the low motion zone of the wearer and which provides expansion of the absorbent article at those portions not fitting within the low motion zone.

Belt

Figure 3:
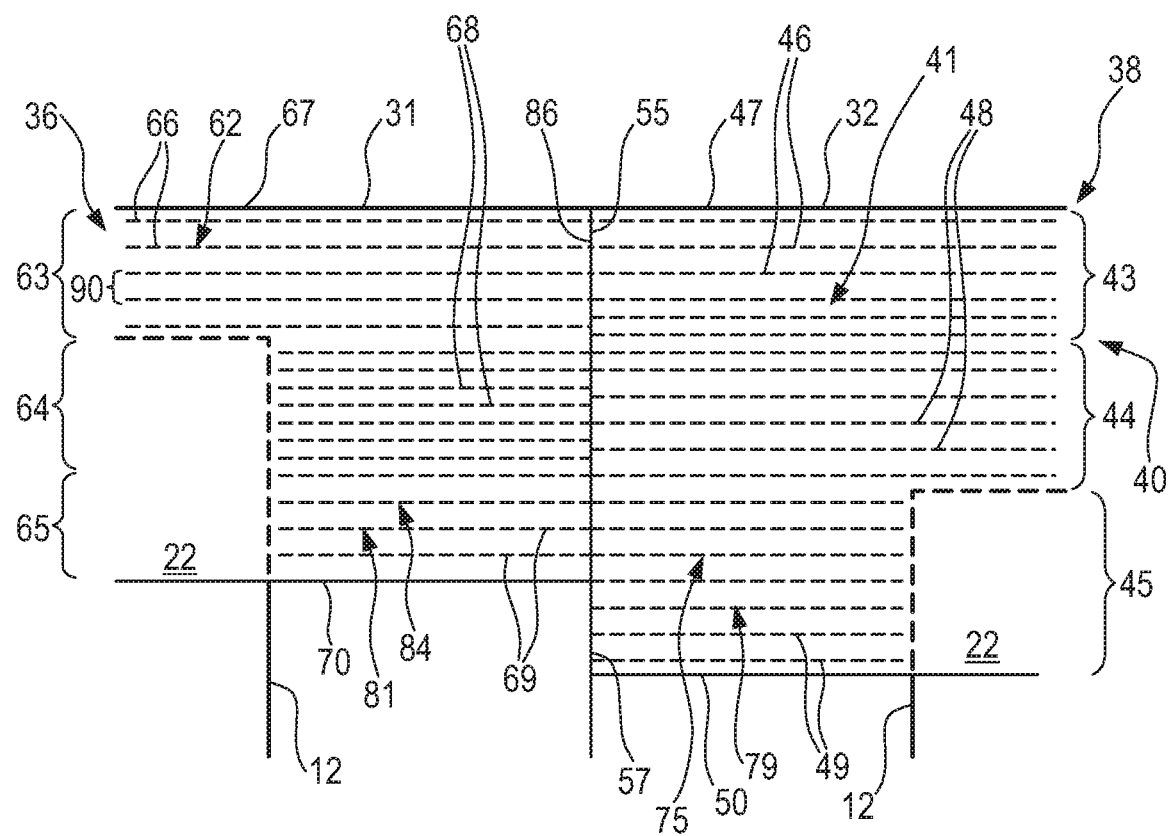
FIG. 3 is an enlarged view of a pars of a first and second belt attached to each other by a side seam plan.
Figure 4:
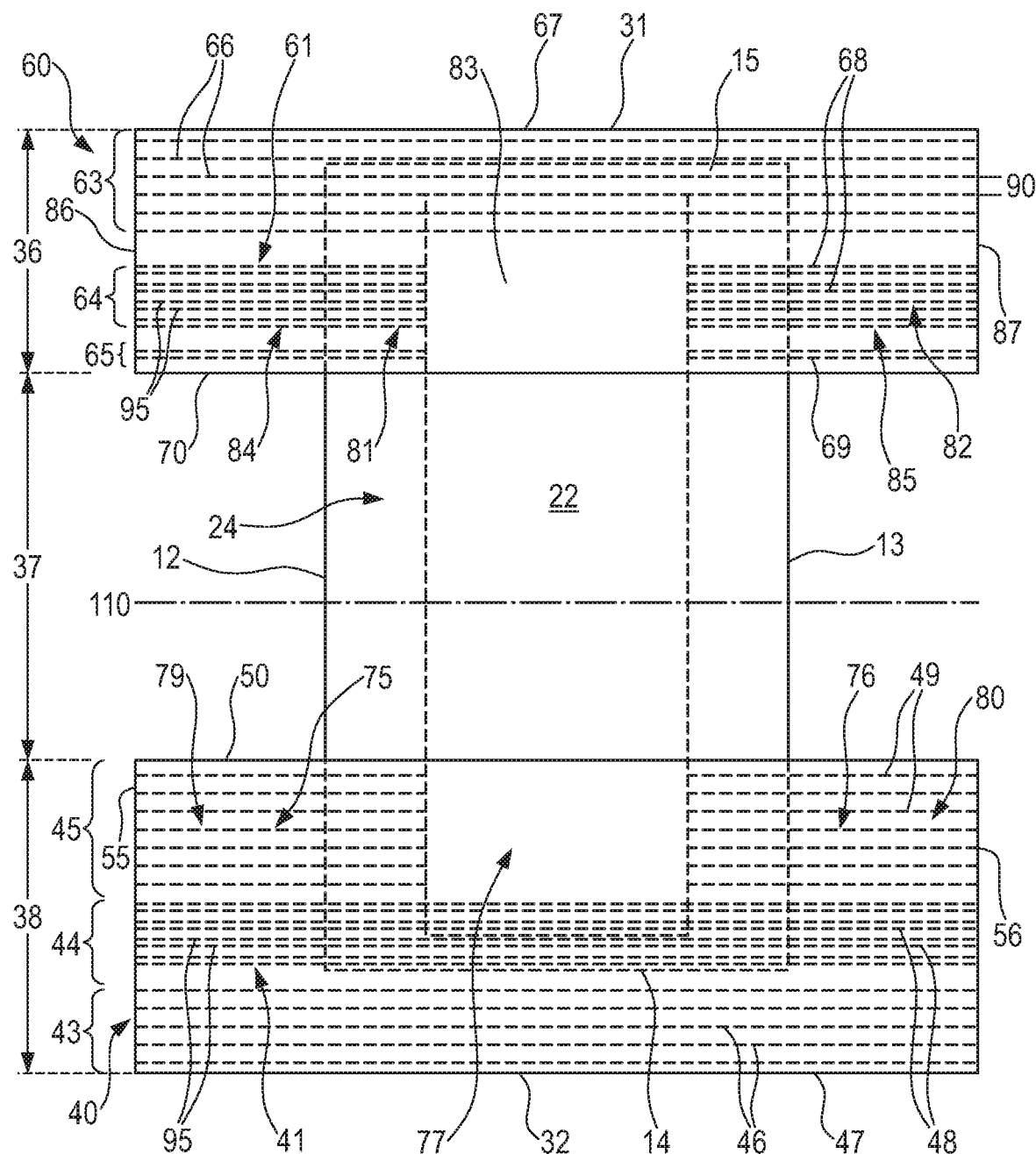
FIG. 4 is a plan view of another exemplary absorbent article of the present disclosure, laid out flat.
Figure 5:
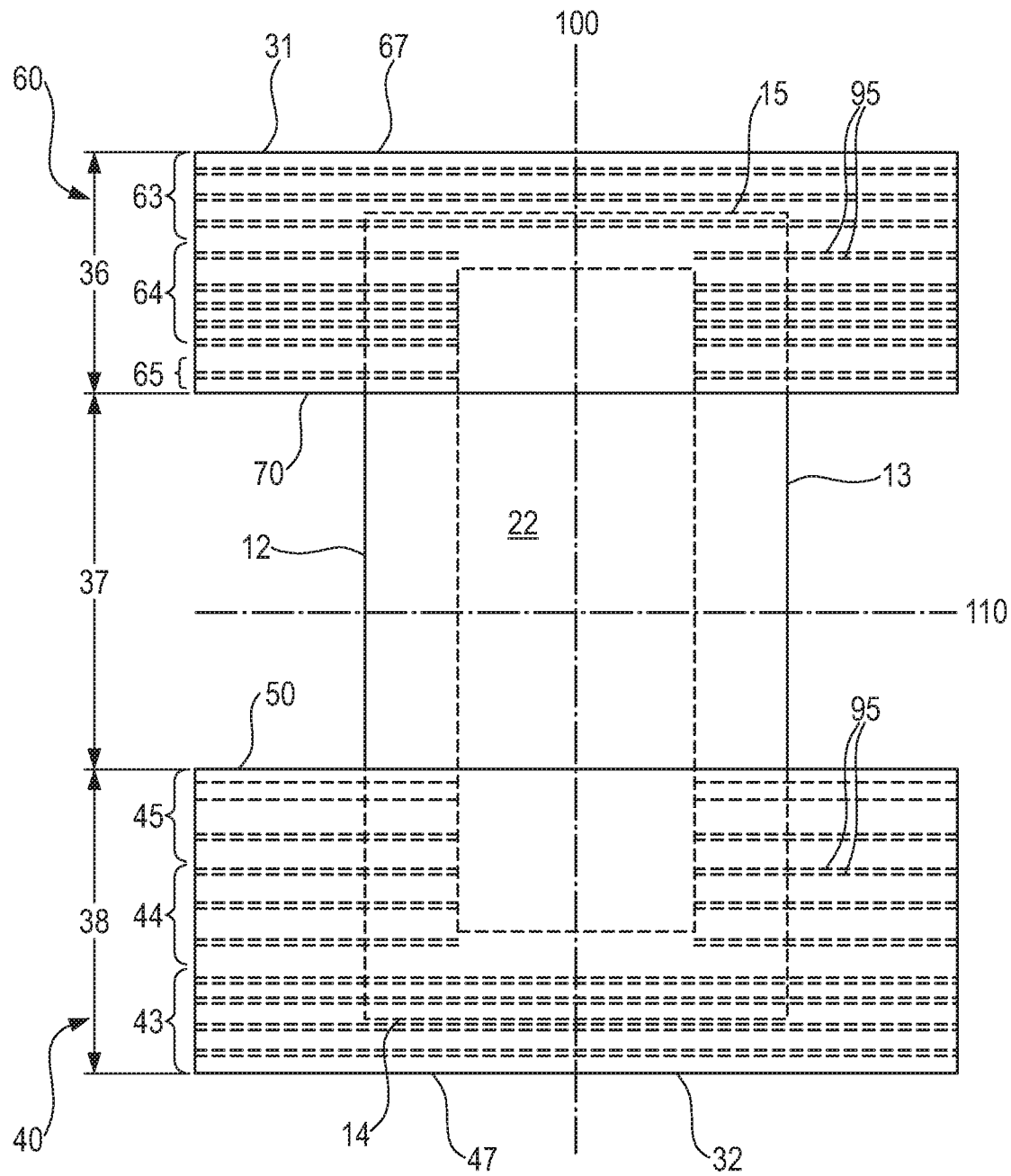
FIG. 5 is a plan view of still another exemplary absorbent article of the present disclosure, laid out flat.
Figure 6:
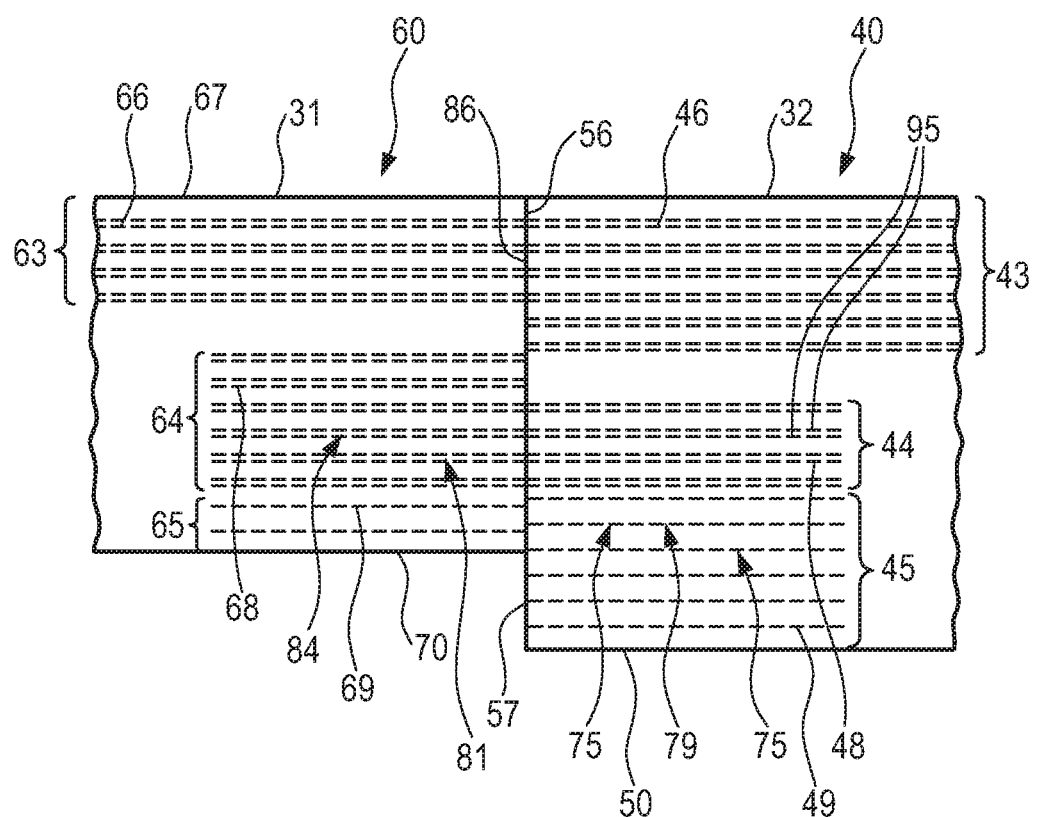
FIG. 6 is an enlarged view of a parts of a first and second belt attached to each other by a side seam plan.
Figure 7:
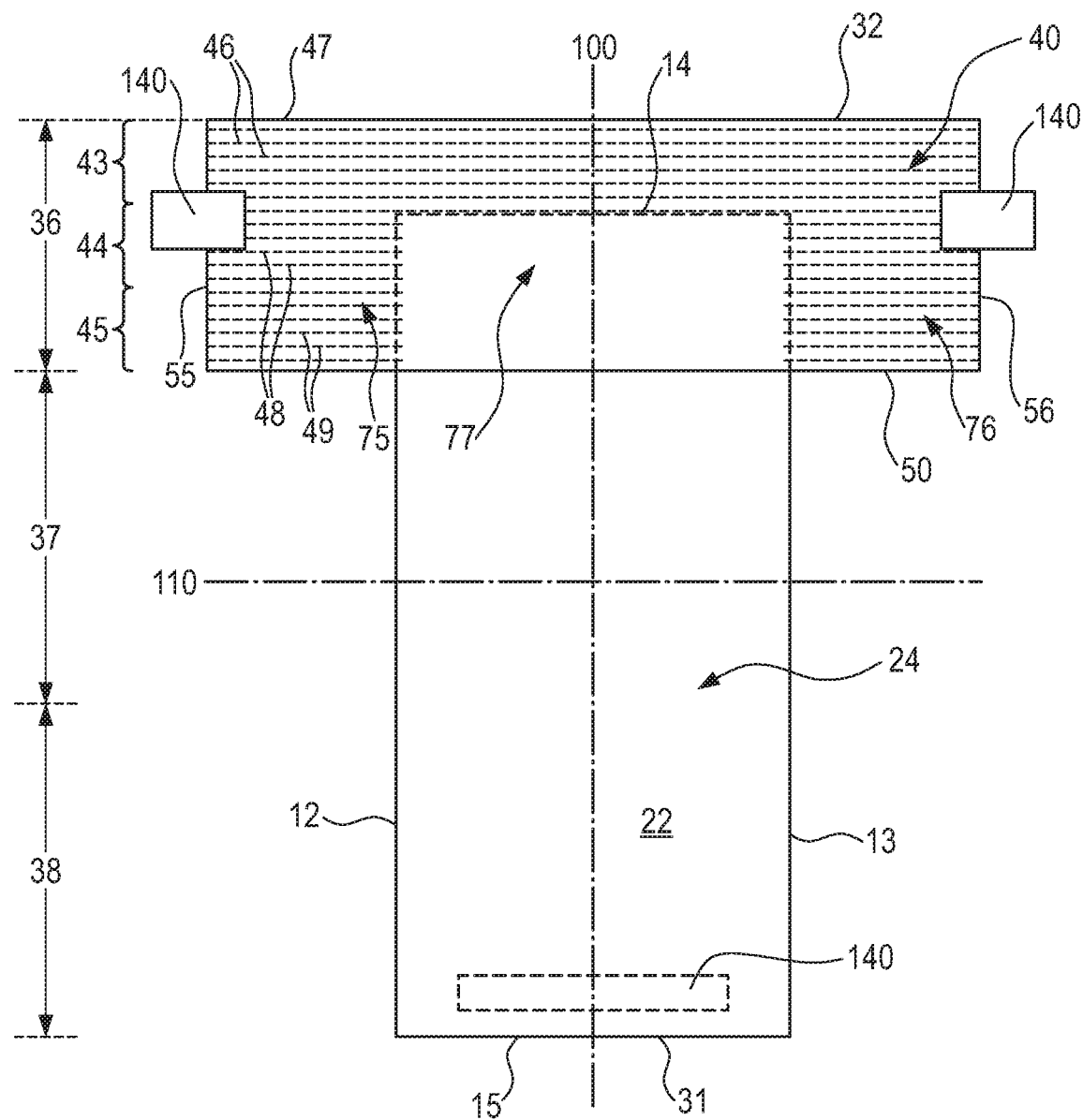
FIG. 7 is a plan view of another exemplary absorbent article having only a first belt, laid out flat.

In addition to FIGS. 1, 2, 4, 5, 7 and 8, which show absorbent articles of the present disclosure including the belt(s), FIGS. 3 and 6 show enlarged views of parts of a first and second belt being joined to each other at a side seam.

The absorbent article 20 of the present disclosure comprises at least a first belt 40. The first belt 40 may be provided in the rear waist region 38. Here, the first belt 40 forms the rear waist edge 32 of the absorbent article 20. The absorbent article 20 may further comprise a second belt 60 which is provided in the front waist region 36. For such absorbent articles 20, the second belt 60 forms the front waist edge 31 of the absorbent article 20.

The first belt 40 comprises a first belt layer 41 disposed on an interior (i.e. body-facing) surface of the first belt 40, a second belt layer 42 disposed on an exterior (i.e. garment-facing) surface of the first belt 40.

The optional second belt 60 comprises a third belt layer 61 disposed on an interior (i.e. body-facing) surface of the second belt 60, a fourth belt layer 62 disposed on an exterior (i.e. garment-facing) surfaces of the second belt 60.

The first and the optional second belt 40, 60 further comprise elastic strands 200 extending substantially along the transverse direction of the absorbent article 20. The elastic strands 200 of the first belt 40 are disposed between the first and second belt layer 41 and 42. The elastic strands 200 of the optional second belt 60 are disposed between the third and fourth belt layer 61 and 62.

The transverse direction extends parallel to the transverse centerline 110 of the absorbent article 20. As used herein, elastic strands 200 extending "substantially" along the transverse direction include deviations from the transverse direction where the elastic strands extend at an angle of up to 30°, or up to 20°, or up to 15°, or up to 10°, or up to 5° from the transverse centerline. Substantially along the transverse direction also includes parallel to the transverse direction (with no deviation).

The elastic strands 200 extending substantially along the transverse direction may extend straight, i.e. they extend along a straight line. Alternatively, the elastic strands 200 extending substantially along the transverse direction may be curved such that they at least twice intersect a line that is parallel or angled (up to 30°, or up to 20°, or up to 15°, or up to 10°, or up to 5°) to the transverse centerline of the absorbent article.

The elastic strands 200 may also be provided as a combination of the above executions such that, for example, some of the elastic strands 200 extend straight and parallel to the transverse centerline while others extend curved and at an angle to the transverse centerline 110.

The determination whether the elastic strands 200 extend substantially along the transverse direction is made while the respective belt layers are flat and straightened out with the elastic strands being in a stretched state.

The first belt layer 41 and the second belt layer 42 may each be made of one continuous sheet of material (which may be a single layer material or a laminate). Alternatively, the first and/or second belt layer 41 and 42 may each be made of more than one sheet of material which are joined to each other along portions of their perimeter to form the first and the second belt layer 41 and 42, respectively. The first and second belt layer 41 and 42 may also be formed by folding over a continuous sheet of material (which may be a single layer material or a laminate) at the rear waist edge 32. Also, a continuous sheet of material (which may be a single layer material or a laminate) may be folded over at the front waist edge 32 and forming the complete second belt layer 42 and portions of the first belt layer 41, wherein the one or more other continuous sheet(s) of material (which may each be a single layer material or a laminate) is/are joined to the portion of the first belt layer that is continuous with the second front belt layer and formed by being folded over.

Likewise, the third and fourth belt layer 61 and 62 of the optional second belt 60 may each be made of one continuous sheet of material (which may be a single layer material or a laminate). Alternatively, the optional third and/or fourth belt layer 61 and 62 may each be made of more than one sheet of material which are joined to each other along portions of their perimeter to form the third and fourth belt layer, respectively. The third and fourth belt layer 61 and 62 may also be formed by folding over a continuous sheet of material (which may be a single layer material or a laminate) at the front waist edge 31. Also, a continuous sheet of material (which may be a single layer material or a laminate) may be folded over at the front waist edge 31 and forming the complete fourth belt layer 62 and portions of the third belt layer 61, wherein the one or more other continuous sheet(s) of material (which may each be a single layer material or a laminate) is joined to the portion of the third belt layer that is continuous with the fourth belt layer and formed by being folded over.

Belt Layers

The first, second, as well as the optional third and fourth belt layer 41, 42, 61 and 62 may be non-extensible, non-elastic or highly-non-elastic. They may be formed from nonwoven webs, woven webs, knitted fabrics, polymeric films, apertured polymeric films, sponges, foams, scrims, and combinations and laminates thereof.

Nonwoven webs used to form the belt layers 41, 42, 61 and 62 can be formed by direct extrusion processes during which the fibers and webs are formed at about the same point in time, or by preformed fibers which can be laid into webs at a distinctly subsequent point in time.

Example direct extrusion processes include but are not limited to: spunbonding, spunlaid, meltblowing, solvent spinning, electrospinning, carded, film fibrillated, melt-film fibrillated, airlaid, dry-laid, wet-laid staple fibers, and combinations thereof typically forming layers.

Example "laying" processes include wetlaying and drylaying. Example drylaying processes include but are not limited to airlaying, carding, and combinations thereof. Example combinations include but are not limited to spunbond-meltblown-spunbond (SMS), spunbond-carded (SC), spunbond-airlaid (SA), meltblown-airlaid (MA), and combinations thereof, typically in layers. The fibers in a nonwoven web are typically joined to one or more adjacent fibers at some of the overlapping junctions. This includes joining fibers within each layer and joining fibers between layers when there is more than one layer. Fibers can be joined by mechanical entanglement (such as pressure bonding, thermal bonding, chemical bonding or by combinations thereof.

In some embodiments, nonwoven fabric can be electrospun nonwoven webs, flashspun nonwoven webs (e.g., Tyvek™ by DuPont), or combinations thereof.

The nonwoven webs used for the first and second and optional third and fourth—belt layers can be made of polyolefin fibers, such as polypropylene (PP) or polyethylene (PE), blends of PP and PE; polyesters, polyamides, polyurethanes, rayon, cellulose, copolymers thereof, or blends or mixtures thereof. The nonwoven webs of the belt layers may also be made of poly-lactic acid (PLA), polyethylene terephthalate (PET) and/or blends or mixtures thereof.

The nonwoven webs used for the first and second—and optional third and fourth—belt layers 41, 42, 61 and 62 can also comprise fibers that are homogenous structures i.e. the fibers are monocomponent fibers; or comprise bicomponent fibers, which may have sheath/core, side-by-side, islands-in-the-sea, and other bicomponent configurations.

For nonwoven webs used as belt layers 41, 42, 61 and 62 and made of bicomponent or multi-component fibers, one of the components of the fibers, preferably the outer component, may be a soft polymer, such as polyethylene or elastic polyolefin, elastic polyurethane. For example, in a sheath/core bi-component fiber, the sheath can be made of polyethylene while the core can be made of polypropylene. Often, the individual components comprise polyolefins such as polypropylene or polyethylene, or their copolymers, polyesters, thermoplastic polysaccharides or other biopolymers. In some embodiments, a nonwoven may be a PE/PET (polyethylene/polyethylene terephthalate) core/sheath bicomponent material, wherein the core is the PET and the outer sheath is PE.

The nonwoven webs of the belt layers may include as additives or modifiers, components such as aliphatic polyesters, thermoplastic polysaccharides, or other biopolymers.

One or more of the first and second belt layer 41 and 42 and of the optional third and fourth belt layer 61 and 62 may be apertured. Using a nonwoven web that has been apertured in the manner described below to form one or both of first and second belt layers and/or one or both of the third and fourth belt layer can provide attractive and interesting effects. The apertures and the material surrounding them interact with the contraction-induced rugosities in the first and optional second belt as the belt is moved and stretched as, for example, during wear. Apertures in the first (or third) belt layer will open, close, change shape and shift relative the second (or fourth) belt layer, providing a visual impression of complexity, depth and added texture.

Additionally, the pattern of the apertures may be substantially similar or identical to the pattern of the pre-bonds (if present), in one or more of machine-direction spacing, cross-direction spacing, aperture shape and aperture size. For example, a pattern of pre-bonds may have substantially similar machine and cross direction spacing as the pattern of apertures. Using respective patterns of pre-bonds and apertures that are substantially similar in one or more respects noted can help give the material a more uniform, orderly and/or coherent appearance, and may also help enhance tensile strength as compared with a web in which respective patterns of pre-bonds and apertures do not have such similarities.

Elastic Strands

The elastic strands 200 used for the first and optional second belt 40 and 60 may have a variety of cross sectional shapes, including but not limited to a circle, oval, triangle or square, and may be formed of a variety of materials for example natural rubber and/or lycra. The materials may also comprise a variety of cross sectional areas also known as Dtex or denier.

Belt with Zones

The first belt 40 of the present disclosure comprises a first, second and third belt zone 43, 44 and 45. The first zone 43 is provided adjacent to and including the rear waist edge 32 of the absorbent article 20 (i.e. it includes the rear waist edge 32 and extends towards the transverse centerline 110 of the absorbent article). The second zone 44 is provided between the first and the third zone 43 and 45 in transverse direction of the absorbent article. Thus, the second zone 44 is disposed more proximal to the transverse centerline 110 than the first zone 43, and the third zone 45 is disposed more proximal to the transverse centerline 110 than the first and second zone 43 and 44.

Each of the first, second and third zone 43, 44, and 45 comprises elastic strands 200 which extend substantially along the transverse direction of the absorbent article 20 and which are disposed between the first and second belt layer 41 and 42.

The second zone 44 can generally provide higher stress and thus sustained fit within the low motion zone of a wearer while the first and third zone 43 and 45 can be provided outside the low motion zone with lower stress. This leads to increased wearer comfort and reduced red-marking of the skin due to the specific configuration of the elastic strands provided in each of the first, second and third zones 43, 44, and 45.

The elastic strands 200 of the first zone 43 comprise a first plurality of elastic strands 46 which are attached to one or both of the first and second belt layer 41, 42 at or adjacent the transversally opposing ends of the respective elastic strand of the first plurality of elastic strands 46. The elastic strands of the first plurality of elastic strands 46 may not be attached to the first and second belt layer 41, 42 in any other location apart from the location at or adjacent to their transversal opposing ends. Alternatively, the elastic strands may be attached at intervals to the first and/or second belt layer 41, 42 which are between their attachments at or adjacent their opposing ends.

The elastic strands 200 of the third zone 45 comprise a third plurality of elastic strands 49 which are attached to one or both of the first and second belt layer 41, 42 at or adjacent the transversal opposing ends of the respective elastic strand of the third plurality of elastic strands 49. The elastic strands of the third plurality of elastic strands 49 may not be attached to one or both of the first and second belt layer 41, 42 in any other location apart from the location at or adjacent to their transversally opposing ends. Alternatively, the elastic strands may be attached at intervals to the first and/or second belt layer 41, 42 which are between their attachments at or adjacent their opposing ends.

Attaching the elastic strands of the first and/or third plurality of elastic strands 46, 49 only at or adjacent their respective opposing ends leads to elastic strands which are free to expand and contract in the transverse direction of the absorbent article 20 without being constrained in their movement due to their attachment to the first and/or second belt layer 41, 42. This results in elastic strands requiring lower force to expand compared to the same elastic strands being attached to the first and/or second belt layer. Hence, such attachment can lead to improved comfort for the wearer, ease of application and transversal expansion of the first belt during use to accommodate to changes of body shape (e.g. due to movement of the wearer, or expansion of the belly).

Additionally attaching the elastic strands of the first and/or third plurality of elastic strands 46, 49 to the first and/or second layer at intervals between their attachments at or adjacent their opposing ends can be done to adjust and control the force needed to elongate the elastic strands. The intervals should be large enough to provide a relatively high degree of freedom for the elastic strands to expand without constrains. Thus, the intervals between neighboring attachments of the elastic strands of the first and/or third plurality of elastic strands to the first and/or second belt layer 41, 42 may be at least 20%, or at least 30%, or at least 40% of the overall length of the elastic strand, when the elastic strand is in its relaxed, contracted state.

The first and second belt layers 41, 42 are joined to each other between neighboring pairs of elastic strands of the first plurality of elastic strands 46 in the first zone 43 (not shown in the Figures).

The first and second belt layers 41, 42 are also joined to each other between neighboring pairs of elastic strands of the third plurality of elastic strands 49 in the third zone 45 (not shown in the Figures).

Due to the attachment to the first and/or second belt layer 41, 42 between neighboring pairs of elastic strands, the elastic strands are substantially held in their position relative to the longitudinal dimension of the absorbent article 20, i.e. they can only move to a limited extent in the longitudinal dimension of the absorbent article 20, without a need to attach the elastic strands to the first and/or second belt layer across all its length extending in the transverse direction. The attachment to the first and/or second belt layer between neighboring pairs of elastic strands also supports the overall integrity of the first belt, avoiding that the first and second layer are separated from each other in the first and third zone, which may lead to undesirable shifting of the layers relative to each other in these areas. Thereby, fit is comfort can be maintained during use of the absorbent article.

The elastic strands of the second zone 44 comprise a second plurality of elastic strands 48 which are attached to one or both of the first and second belt layers 41, 42 along substantially the complete length of the elastic strands in transverse direction of the absorbent article 20. The term "substantially the complete length" includes attachment along the complete length but also includes attachment with unsubstantial gaps where the elastic stands of the second plurality of elastic strands remain unattached to the first and second belt layer 41, 42. Such unsubstantial gaps are gaps which are less than 5%, or less than 3%, or less than 2% of the overall length of the elastic strand, when the elastic strand is in its relaxed, contracted state.

Allowing for such unsubstantial gaps, allows for minor process variations when attaching the elastic strands to the first and/or second belt layer 40, 60.

When the absorbent article 20 of the present disclosure comprises a second belt 60, the second belt 60 comprises a fourth, fifth and sixth belt zone 63, 64 and 65. The fourth zone 63 is provided adjacent to and including the front waist edge 31 (i.e. it includes the front waist edge 31 and extends towards the transverse centerline 110 of the absorbent article 20). The fifth zone 64 is provided between the fourth and the sixth zone 63 and 65 in transverse direction of the absorbent article 20. Thus, the fifth zone 64 is disposed more proximal to the transverse centerline 110 than the fourth zone 63, and the sixth zone 65 is disposed more proximal to the transverse centerline 110 than the fourth and fifth zone 63 and 64.

Each of the fourth, fifth and sixth zone 63, 64 and 65 comprises elastic strands 200 which extend substantially along the transverse direction of the absorbent article 20 and which are disposed between the third and fourth belt layer 61 and 62.

Similar to the first belt 40, if the absorbent article 20 comprises a second belt 60, the fifth zone 64 can generally provide higher stress and thus sustained fit within the low motion zone of a wearer while the fourth and sixth zone 63 and 65 can be provided outside the low motion zone with lower stress outside the low motion zone to increase wearer comfort and reduce red-marking of the skin due to the specific configuration of the elastic strands provided in each of the fourth, fifth and sixth zones 63, 64 and 65.

The elastic strands of the fourth zone 63 comprise a fourth plurality of elastic strands 66 which are attached to one or both of the third and fourth belt layer 61, 62 at or adjacent the transversally opposing ends of the respective elastic strand of the fourth plurality of elastic strands 66. The elastic strands of the fourth plurality of elastic strands 66 may not be attached to one or both of the third and fourth belt layer 61, 62 in any other location apart from the location at or adjacent to their transversally opposing ends. Alternatively, the elastic strands may be attached at intervals to the third and/or fourth belt layer 61, 62 which are between their attachments at or adjacent their opposing ends.

The elastic strands of the sixth zone 65 comprise a sixth plurality of elastic strands 69 which are attached to one or both of the third and fourth belt layer 61, 62 at or adjacent the transversally opposing ends of the respective elastic strand of the sixth plurality of elastic strands 69. The elastic strands of the sixth plurality of elastic strands 69 may not be attached to the third and fourth belt layer 61, 62 in any other location apart from the location at or adjacent to their transversally opposing ends. Alternatively, the elastic strands may be attached at intervals to the third and/or fourth belt layer 61, 62 which are between their attachments at or adjacent their opposing ends.

Attaching the elastic strands of the fourth and/or sixth plurality of elastic strands 66, 69 only at or adjacent their respective opposing ends leads to elastic strands which are free to expand and contract without being constrained in their movement due to their attachment to the third and/or fourth belt layer 61, 62. This results in elastic strands requiring lower force to expand compared to the same elastic strands being attached to the third and/or fourth belt layer. Hence, such attachment can lead to improved comfort for the wearer, ease of application and transversal expansion of the second belt 60 during use to accommodate to changes of body shape (e.g. due to movement of the wearer, or expansion of the belly).

Additionally attaching the elastic strands of the fourth and/or sixth plurality of elastic strands 66, 69 to the third and/or fourth layer 61, 62 at intervals between their attachments at or adjacent their opposing ends can be done to adjust and control the force needed to elongate the elastic strands. The intervals should be large enough to provide a relatively high degree of freedom for the elastic strands to expand without constrains. Thus, the intervals between neighboring attachments of the elastic strands of the fourth and/or sixth plurality of elastic strands 66, 69 to the third and/or fourth belt layer 61, 62 may be at least 20%, or at least 30%, or at least 40% of the overall length of the elastic strand, when the elastic strand is in its relaxed, contracted state.

The third and fourth belt layers 61, 62 are joined to each other between neighboring pairs of elastic strands of the fourth plurality of elastic strands 66 in the fourth zone 63 (not shown in the Figures).

The third and fourth belt layers 61, 62 are also joined to each other between neighboring pairs of elastic strands of the sixth plurality of elastic strands 69 in the sixth zone 65 (not shown in the Figures).

Due to the attachment to the third and/or fourth second belt layer 61, 62 between neighboring pairs of elastic strands, the elastic strands are substantially held in their position relative to the longitudinal dimension of the absorbent article 20, i.e. they can only move to a limited extent in the longitudinal dimension of the absorbent article, without a need to attach the elastic strands to the first and/or second belt layer 61, 62 across all its length extending in the transverse direction. The attachment to the third and/or fourth belt layer between neighboring pairs of elastic strands also supports the overall integrity of the second belt, avoiding that the third and fourth layer are not separate from each other in the fourth and sixth zone, which may lead to undesirable shifting of the layers relative to each other in these areas. Thereby, fit is comfort can be maintained during use of the absorbent article.

The elastic strands of the fifth zone 64 comprise a fifth plurality of elastic strands 68 which are attached to one or both of the third and fourth belt layers 61, 62 along substantially the complete length of the elastic strands in transverse direction of the absorbent article 20. The term "substantially the complete length" includes attachment along the complete length but also includes attachment with unsubstantial gaps where the elastic stands of the fifth plurality of elastic strands 64 remain unattached to the third and fourth belt layer 61, 62. Such unsubstantial gaps are gaps which are less than 5%, or less than 3%, or less than 2% of the overall length of the elastic strand, when the elastic strand is in its relaxed, contracted state.

Allowing for such unsubstantial gaps, allows for minor process variations when attaching the elastic strands to the third and/or fourth belt layer 61, 62.

Attachment of the elastic strands of one or more (or all of) the first, second, third, and the optional fourth, fifth and sixth pluralities of elastic strands to the first and/or second belt layer, or to the third and fourth belt layer, respectively, may be done adhesively. Adhesive attachment is preferred over e.g. ultrasonic attachment, as the elastic properties of the elastic strands are negatively impacted to a lesser extent by use of adhesive. Adhesive attachment of elastic strands to nonwoven layers in order to make elastic laminates is generally well known in the art.

The elastic strands within each of the first, second, third, and the optional fourth, fifth and sixth pluralities of elastic strands may be spaced apart from their respective neighboring elastic strand in the longitudinal direction of the absorbent article by 2 to 15 mm, or from 2 to 10 mm, or from 3 to 10 mm, or from 4 to 10 mm (these values relate to the gap 90 between neighboring elastic strands). The spacing 90 between neighboring elastic strands in the longitudinal absorbent article direction may be the same in each of the first, second, third, and the optional fourth, fifth and sixth pluralities of elastic strands. Alternatively, one or more plurality of elastic strands may have elastics which have a greater distance between neighboring elastic strands than the elastic strands of one or more other plurality of elastic strands. For example, it may be desirable to provide neighboring elastic strands in the second plurality of elastic strands and, if present, in the fifth plurality of elastic strands with a smaller distance between them, compared to the elastic strands in the first, third and, if present, the fourth and sixth plurality of elastic strands. That may, a better, closer fit to the body of the wearer can be obtained in the second and the optional fifth zone.

The gap from the elastic strands of the first plurality of elastic strands to the elastic strands of the second plurality of elastic strands (i.e. the spacing between the most proximate—to the transverse centerline—elastic strand of the first plurality of elastic strands to the most distal—to the transverse centerline—elastic strand of the second plurality of elastic strands) may be the same as the spacing between neighboring elastic strands of the first and/or second plurality of elastic strands. Alternatively, the gap from the elastic strands of the first plurality of elastic strands to the elastic strands of the second plurality of elastic strands may be wider than the spacing between neighboring elastic strands of the first and/or second plurality of elastic strands to provide for more distinct first and second zone.

The same applies for the gap from the elastic strands of the second plurality of elastic strands to the elastic strands of the third plurality of elastic strands (i.e. the spacing between the most proximate—to the transverse centerline—elastic strand of the second plurality of elastic strands to the most distal—to the transverse centerline—elastic strand of the third plurality of elastic strands) may be the same as the spacing between neighboring elastic strands of the second and/or third plurality of elastic strands. Alternatively, the gap from the elastic strands of the second plurality of elastic strands to the elastic strands of the third plurality of elastic strands may be wider than the spacing between neighboring elastic strands of the second and/or third plurality of elastic strands to provide for more distinct second and third zone.

Likewise, if the absorbent article comprises a second belt, the gap from the elastic strands of the third plurality of elastic strands to the elastic strands of the fourth plurality of elastic strands (i.e. the spacing between the most proximate—to the transverse centerline—elastic strand of the fourth plurality of elastic strands to the most distal—to the transverse centerline—elastic strand of the fifth plurality of elastic strands) may be the same as the spacing between neighboring elastic strands of the fourth and/or fifth plurality of elastic strands. Alternatively, the gap from the elastic strands of the fourth plurality of elastic strands to the elastic strands of the fifth plurality of elastic strands may be wider than the spacing between neighboring elastic strands of the fourth and/or fifth plurality of elastic strands to provide for more distinct fourth and fifth zone.

Also, for absorbent articles comprising a second belt, the gap from the elastic strands of the fifth plurality of elastic strands to the elastic strands of the sixth plurality of elastic strands (i.e. the spacing between the most proximate—to the transverse centerline—elastic strand of the fifth plurality of elastic strands to the most distal—to the transverse centerline—elastic strand of the sixth plurality of elastic strands) may be the same as the spacing between neighboring elastic strands of the fifth and/or sixth plurality of elastic strands. Alternatively, the gap from the elastic strands of the fifth plurality of elastic strands to the elastic strands of the sixth plurality of elastic strands may be wider than the spacing between neighboring elastic strands of the fifth and/or sixth plurality of elastic strands to provide for more distinct fifth and sixth zone.

Some of the elastic strands 200 of the first belt 40 and/or the optional second belt 60 may be arranged in sets of elastic strands 200 which are longitudinally spaced apart from each other to lesser extends than the other elastic strands 200 in the first and/or second belt 40, 60, thereby forming concentrated arrays of elastic strands 95. A concentrated array 95 may comprise 2 to 4 elastic strands, or 3 to 4 elastic strands. Such concentrated arrays 95 are preferably formed by elastic strands of the second plurality of elastic strands 48 and/or of the fifth plurality of elastic strands 68. The longitudinal spacing 90 between elastic strands in concentrated arrays 95 may be from 2-4 mm, whereas the longitudinal spacing 90 between the other elastic strands may have a longitudinal spacing 90 larger than 4 mm, such as 5 to 10 mm, or 6-10 mm.

Without being bound by theory, by disposing the elastic strands 200 in such close proximity to each other, the concentrated array 95 exhibits a behavior as if it was one elastic strand with a certain width, and provides various benefits. For example, the concentrated array 95 provides more or less the combined tensile force of the elastic strands in the concentrated array 95, such that each elastic strand 200 may be disposed at a much lower tensile force. Further, the gathers 130 created in the gap 90 between elastic strands 200 of the concentrated array 95 are so fine that the area of the first belt layer—and/or the optional third belt layer—facing the body is significantly increased. Such increased area of material, combined with the elastic strands of the concentrated array, apply a tensile force to the wearer over a distributed width, compared to the width of a single elastic strand. Namely, the concentrated array exhibits a behavior as if it were one elastic body. As such, the concentrated array may provide a good fit to the wearer by using relatively low density elastic strands which are economically supplied. The reduction of tensile force in a concentrated area compared to that of a single elastic strand may also reduce red marking on the skin of the wearer, and provide the wearer with a more comfortable and soft fit. Further, a concentrated array may provide the appearance of an elastic body of a certain width, similar to elastic bodies disposed on a durable undergarment. Thus, provision of a concentrated array may connote an undergarment look, or high quality.

A concentrated array 95 may provide more or less the combined tensile force of the elastic strands 200 in the concentrated array, such that each elastic strand may be disposed at a relatively lower tensile force. The elastic strands for forming a concentrated array may have a density of no more than 1100 dtex, or no more than 940 dtex, and disposed at an elongation of from 150% to 300%.

Concentrated arrays 95 may be provided in zones for which higher tensile stress is desired. The provision of at least two concentrated arrays may be particularly effective. At least two concentrated arrays may be provided in the second zone. At least two concentrated arrays may be provided in the optional fifth zone. The tensile stress of the fifth zone, if present, may be provided higher than the tensile stress of any other zone. The first and third, and the optional fourth and sixth zone may or may not comprise concentrated arrays. The number of concentrated arrays in the second and in the optional fifth zone may be higher than the number of concentrated arrays in the first and third, and the optional fourth and sixth zone.

Attachment of the first belt layer 41 to the second belt layer 42 between neighboring pairs of elastic strands of the first and third plurality of elastic strands 46 and 49 is desirably done by adhesive. Moreover, attachment of the optional third belt layer 61 to the optional fourth belt layer 62 between neighboring pairs of elastic strands of the fourth and sixth plurality of elastic strands 66, 69 is also desirably done adhesively. Compared to ultrasonic bonding, adhesive bonding can be controlled better. Ultrasonic bonding tends to generate too much heat which irradiates to the area immediately surrounding the ultrasonic bond. This may negatively impact the elastic properties of the elastic strands or may otherwise damage the elastic strands, especially for relatively narrow spacing 90 between neighboring elastic strands, such as spacing below 10 mm, or even below 6 mm.

Also, continuous bonding of the first belt layer 41 to the second belt layer 41 and, if a second belt 60 is used, of the third belt layer 61 to the second belt layer 62 between neighboring pairs of elastic strands of the first, third, optional fourth and sixth pluralities of elastic strands may be continuous, i.e. not intermittent.

The elastic strands 200 are typically disposed between the first and second belt layers 41, 42 while the elastic strands are in an expanded, stretched state. After having been joined to the first and/or second belt layer, the elastic strands are allowed to contract, thus forming corrugations 130 in the first and second belt layer 41, 42. The same applies to the optional second belt 60: The elastic strands 200 are typically disposed between the third and fourth belt layers 61 and 62 while the elastic strands are in an expanded, stretched state. After having been joined to the third and/or fourth belt layer, the elastic strands are allowed to contract, thus forming corrugations 130 in the third and fourth belt layer 61 and 62.

By having a continuous adhesive attachment of the first belt layer 41 to the second belt layer 42 (or, if present, of the third and fourth belt layers 61 and 62, respectively) between neighboring elastic strands of the first and third zone (and fourth and sixth zone, respectively), the corrugations 130 of the first and second belt layer 41, 42 (or the third and fourth belt layer 61, 62, respectively) obtained by contraction of the elastic strands is more homogeneous and uniform. This facilitates a smoother and more uniform appearance of the belt, which provides for more uniform elongation behavior of the belt in the transverse direction and which is generally perceived as being more garment-like.

The first belt 40 has first and a second longitudinal belt side edge 55 and 56 and the optional second belt 60 has a third and a fourth longitudinal belt side edge 86 and 87. The longitudinal belt side edges of the first and the optional second belt may be substantially parallel to the longitudinal centerline 110 of the absorbent article 20.

The first belt 40 also has a first and a second transverse belt end edge 47 and 50 and the optional second belt 60 has third and fourth transverse belt end edge 67 and 70. If the first belt 40 is provided in the rear waist region 38 the first transverse belt end edge 47 of the first belt 40 forms the rear waist edge 32 of the absorbent article 20. If the absorbent article 20 comprises a second belt 60, the third transverse belt end edge 67 of the second belt 60 forms the front waist edge 31 of the absorbent article 20. The first transverse belt end edge 47 of the first belt 40 may be substantially straight. The second transverse belt end edge 50 of the first belt 40 may be substantially straight or may be curved. The second transverse belt end edge 50 may form a portion of the leg openings when the absorbent article 20 is applied onto the wearer (or if the absorbent article is a pant with preformed leg openings).

Likewise, the third transverse belt end edge 67 of the second belt 60, if present, may be substantially straight and/or the fourth transverse belt end edge 70 of the second belt 60 may be substantially straight or may be curved. The fourth transverse belt end edge 70 may form a portion of the leg openings when the absorbent article 20 is applied onto the wearer (or if the absorbent article is a pant with preformed leg openings).

For example, those portions of the second transverse belt end edge 50 of the first belt 40 and, those portions of the fourth transverse belt end edge 70 of the optional second belt 60, which contribute to the formation of the leg openings of the absorbent article 20, may have an arcuate shape such that the first and the optional second belt 40, 60 have their smallest longitudinal dimension (parallel to the longitudinal centerline 100 of the absorbent article 20) at the longitudinal belt side edges 55, 56, 86, 87. In such a configuration, the central portion of the second transverse belt end edge 50 of the first belt 40 and the central portions of the fourth transverse belt end edge 70 of the optional second belt 60 which overlap the absorbent core may be straight (determined when the elastic strands are stretched and the belt layers are flattened out).

The shape of the first and the optional second belt is determined by stretching out the respective belt such that the first and second belt layers—or the third and fourth belt layer, respectively—are flat, i.e. have no more folds or corrugations, and the elastic strands are in a stretched condition.

If the absorbent article 20 is a pant and comprises a first and a second belt 40 and 60, the first longitudinal belt side edge 55 of the first belt 40 may be attached to the third longitudinal belt side edge 86 of the second belt 60 to form a first side seam 57. The second longitudinal belt side edge 56 of the first belt 40 may be attached to the fourth longitudinal belt side edge 87 of the second belt 60 to form a second side seam 58. The first and second side seam may be permanent.

The elastic strands of the first, second and third plurality of elastic strands 46, 48 and 49 may differ from each other, and/or the elastic strands of the first, second and third plurality of elastic strands 46, 48 and 49 may be applied differently from each other. For example, any the elastic strands of the first and third plurality of elastic strands 46 and 49 may differ from the elastic strands of the second plurality of elastic strands 48 in any of a) strain of the elastic strands, b) distance between neighboring elastic strands, c) number of elastic strands forming the plurality of elastic strands, d) denier of the elastic strands or e) a combination of two or more of a) to d). By way of example, different elastic strands may be provided for the first, second and/or third plurality of elastic strands, or the same elastic strands may be provided in the first, second and third plurality of elastic strands but the respective pluralities of elastic strands may be applied in a different manner (i.e. different in another, additional manner to the elastics of the first and third plurality of elastic strands 46 and 49 being attached to the first and/or second belt layer 41, 42 at or adjacent to their transversally opposing ends and the elastics of the second plurality of elastic strands 48 being attached along substantially their complete length to the first and/or second belt layer 41, 42).

That way, the properties in the first, second and third zone 43, 44 and 45 can be adapted further. For example, the first and third zone 43 and 45 may have lower strain compared to the second zone 44. Thereby, the second zone can be further configured to fit more tightly on the wearer while the first and third zone can provide increased freedom of movement for the wearer and reduced red-marking on the skin.

The first zone 43 may have a first transverse peak extension force, the second zone 44 may have a second transverse peak extension force, and the third zone 45 may have a third transverse peak extension force. The second transverse peak extension force may be greater than one or both of the first and third transverse peak extension force. The second transverse peak extension force may be at least 25% higher, or at least 30% higher, or at least 40% higher, or at least 50% higher than one or both of the first and third transverse peak extension forces. The second peak extension force may not be more than 200%, or more than 150%, or more than 100% higher than one or both of the first and third transverse peak extension forces.

At the same time, it may be desirable to have a level of contraction in the transverse direction in the second zone 44 which does not vary more than 250%, or not more than 200%, or not more than 150% from the level of contraction in the transverse direction in the first and third zones 43 and 45.

This can be achieved by attaching the elastic strands of the second plurality of elastic strands 48 to one or both of the first and second belt layer substantially along the complete length of the elastic strands, while attaching the elastic strands of the first and third plurality of elastic strands 46 and 49 to one or both of the first and second belt layer 41, 42 (only) at or adjacent to the transversally opposing ends, or while attaching the elastic strands of the first and third plurality of elastic strands 46 and 49 to one or both of the first and second belt layer 41, 42 (only) at or adjacent to the transversally opposing ends and in intervals of at least 10%, or at least 20% of the complete transverse extension of the elastic strands (measured when the elastic strands are in their relaxed, contracted state).

Generally, a substantially continuous attachment of the elastic strands 200 to one or both of the first and second belt layer 41, 42, leads to an increase in force necessary to expand the elastic strands 200 along the transverse direction of the absorbent article 20 compared to elastic strands which are attached to the first and/or second belt layer 41, 42 only at or adjacent their respective ends (or only at or adjacent their respective ends and in few locations which are relatively far apart from each other, i.e. in relatively large intervals). On the other hand, the level of contraction of substantially continuously attached elastic strands may not differ to a large extend from the level of contraction of elastic strands which are not substantially continuously attached.

Hence, by selecting the way of attachment of the elastic strands 200 accordingly such that they differ between the first and third plurality of elastic strands 46 and 49 versus the second plurality of elastic strands 48, allows the provision of a first belt 40 which has is more tailor-made to provide the desired properties in the low motion zone compared to zones outside the low motion zone.

Absorbent Articles Comprising a First and a Second Belt

In addition to the above, the following relates to a more specific embodiment of the present disclosure wherein the absorbent article comprises a first and a second belt 40 and 60, which may be joined to each other by a first and second permanent side seam 57 and 58.

The first belt 40 may have a greater longitudinal dimension than the second belt 60, as the first belt 40 is intended to cover the buttocks of the wearer.

When the first and second belts 40 and 60 of such an absorbent article 20 (e.g. a pant) are put in an overlapping configuration such that the front and rear waist edges 31 and 32 coincide, e.g. by laying the absorbent article 20 on table, the second zone 44 of the first belt 40 may completely or—more preferably—only partly overlap with the fifth zone 64 of the second belt 60. An overlap which is only partly may result in an absorbent article 20 wherein the second zone 44 extends further towards the transverse centerline 110 of the absorbent article 20 relative to the fifth zone 64. At the same time, the fifth zone 64 may extend further towards the waist edge relative to the second zone 44.

As explained above and as shown in FIG. 9C, due to the anatomy of a wearer, the primary line of tension is disposed at an angle, a, to the horizontal on the body of the wearer (an angle to the transverse direction of the absorbent article). Hence, by having the second zone 44 of the first belt 40 only partly overlapping with the fifth zone 64 of the second belt 60, an anchoring system can be provided, which more suitably takes the anatomy of the wearer into account.

The second zone 44 of the first belt 40 may be longitudinally offset from the rear waist edge 32 of the absorbent article 20 by a first distance L1, and the fifth zone 64 of the second belt 60 may be longitudinally offset from the front waist edge 31 by a second distance L2, wherein the second distance L2 is less than the first distance L1. The first and second distance are measured as the distance from the front and back waist edge, respectively, to the elastic strand of the second and the fifth zone, respectively, which is most distal from the transverse centerline. The exact dimensions of the first and second distances L1 and L2 will naturally depend on the overall size of the belt, so may widely differ between different absorbent articles, as some absorbent articles may be relatively small to fit babies whiles other absorbent articles are dimensioned to fit adults.

The third zone 45 may be disposed at a third dimension L3 longitudinally offset from the rear waist edge 32 which is less than the offset (=fourth dimension L4) from the front waist edge 31 of the sixth zone 65 in the longitudinal dimension. Likewise to the first and second distances L1 and L2, the exact dimensions of the third and fourth distances L3 and L4 will naturally depend on the overall size of the belt, so may widely differ between different absorbent articles, as some absorbent articles may be relatively small to fit babies whiles other absorbent articles are dimensioned to fit adults.

The first zone 43 may have a greater longitudinal dimension than the fourth zone 63. The second zone 44 may have a greater longitudinal dimension than the fifth zone 64. The third zone 45 may have a greater longitudinal dimension than the sixth zone 65.

Some of the elastic strands of the second zone 44 may be severed across the transverse dimension of the absorbent article 20 to form discontinuous elastic strands. Alternatively, all of the elastic strands of the second zone 44 may be severed across the transverse dimension to form discontinuous elastic strands. Moreover, some or all of the elastic strands of the third zone 45 may also be severed across the transverse dimension of the absorbent article 20 to form discontinuous elastic strands.

None of the elastic strands of the first zone 43 may be severed. Alternatively, it may also be desirable to sever some elastic strands of the first zone 43 across the transverse dimension of the absorbent article 20 to form discontinuous elastic strands. However, the elastic strands of the first zone 43 which are most proximate to the rear waist edge 32 may not be severed to provide continuous elasticity around the waist opening.

If some of the elastic strands of the first plurality of elastic strands 46 are severed and/or some or all of the elastic strands of the third plurality of elastic strands 49 are severed, each of the discontinuous elastic strands is attached to one or both of the first and second belt layer (only) at or adjacent to the transversally opposed ends of the discontinuous elastic strand.

The first belt 40 may have a first transverse belt end region 75 adjacent to its first longitudinal belt side edge 55, a second transverse belt region 76 adjacent to its second longitudinal belt side edge 56, and a first central region 77 between the first and second transverse belt region 75 and 76. If some of the elastic strands of the first zone 43, some or all of the elastic strands of the second zone 44, and/or some or all of the elastic strands of the third zone 45 are severed, the first central region 77 may be free of elastic strands and the discontinuous elastic strands from a first and a second segment 79 and 80 in the first and second transverse belt end regions 75 and 76, respectively. The first central region 77 of the first belt 40 may be the region which overlaps with the absorbent core of the center chassis 22.

Likewise, for the second belt 60, some of the elastic strands of the fifth zone 64 may be severed across the transverse dimension of the absorbent article 20 to form discontinuous elastic strands. Alternatively, all of the elastic strands of the fifth zone 64 may be severed across the transverse dimension to form discontinuous elastic strands.

Moreover, some or all of the elastic strands of the sixth zone 65 may also be severed across the transverse dimension of the absorbent article 20 to form discontinuous elastic strands.

None of the elastic strands of the fourth zone 63 may be severed. Alternatively, it may also be desirable to sever some elastic strands of the fourth zone 63 across the transverse dimension of the absorbent article 20 to form discontinuous elastic strands. However, the elastic strands of the fourth zone 63 which are most proximate to the front waist edge 31 may not be severed to provide continuous elasticity around the waist opening.

If some of the elastic strands of the fourth plurality of elastic strands 66 are severed and/or some or all of the elastic strands of the sixth plurality of elastic strands 69 are severed, each of the discontinuous elastic strands is attached to one or both of the third and fourth belt layer 61, 62 (only) at or adjacent to the transversally opposed ends of the discontinuous elastic strand.

The second belt 60 may have a third transverse belt end region 81 adjacent to its third longitudinal belt side edge 86, a fourth transverse belt region 82 adjacent to its fourth longitudinal belt side edge 87, and a second central region 83 between the third and fourth transverse belt region 81 and 82. If some of the elastic strands of the fourth zone 63, some or all of the elastic strands of the fifth zone 64, and/or some or all of the elastic strands of the sixth zone 65 are severed, the second central region 83 may be free of elastic strands and the discontinuous elastic strands from a third and a fourth segment 84 and 85 in the third and fourth transverse belt end regions 81 and 82, respectively. The second central region 83 of the second belt 60 may be the region which overlaps with the absorbent core of the center chassis 22.

The overall number of non-severed elastic strands extending substantially across the complete transverse dimension in the first belt 40 may e higher than the number elastic strands which were severed.

The overall number of non-severed elastic strands extending substantially across the complete transverse dimension in the second belt 60 may be lower than the number elastic strands which were severed. If the absorbent article is a pant with first and second permanent side seams 57, 58, the elastic strands 200 of the first and second belt 40 and 60 may or may not be comprised in the permanent side seams. If the elastic strands are not comprised in the permanent side seams, the elastic strands may have their opposing ends (across transverse dimension of the article) immediately adjacent to the first and second permanent side seams.

The elastic strands of the fourth, fifth and sixth plurality of elastic strands 66, 68 and 69 may differ from each other, and/or the elastic strands of the fourth, fifth and sixth plurality of elastic strands may be applied differently from each other. For example, any the elastic strands of the fourth and sixth plurality of elastic strands may differ from the elastic strands of the fifth plurality of elastic strands in any of a) strain of the elastic strands, b) distance between neighboring elastic strands, c) number of elastic strands forming the plurality of elastic strands, d) denier of the elastic strands or e) a combination of two or more of a) to d). By way of example, different elastic strands may be provided for the fourth, fifth and/or sixth plurality of elastic strands, or the same elastic strands may be provided in the fourth, fifth or sixth plurality of elastic strands but the respective pluralities of elastic strands may be applied in a different manner (i.e. different in another, additional manner to the elastics of the fourth and sixth plurality of elastic strands 66 and 69 being attached to the third and/or fourth belt layer 61, 62 at or adjacent to their transversally opposing ends and the elastics of the fifth plurality of elastic strands 68 being attached along substantially their complete length to the third and/or fourth belt layer 61, 62).

That way, the properties in the fourth, fifth and sixth zone 63, 64 and 65 can be adapted further. For example, the fourth and sixth zone 63 and 65 may have lower strain compared to the fifth zone 64. Thereby, the fifth zone can be further configured to fit more tightly on the wearer while the fourth and sixth zone can provide increased freedom of movement for the wearer and reduced red-marking on the skin.

The fourth zone 63 may have a fourth transverse peak extension force, the fifth zone 64 may have a fifth transverse peak extension force, and the sixth zone 65 may have a sixth transverse peak extension force. The fifth transverse peak extension force may be greater than one or both of the fourth and sixth transverse peak extension force. The fifth transverse peak extension force may be at least 25% higher, or at least 30% higher, or at least 40% higher, or at least 50% higher than one or both of the fourth and sixth transverse peak extension forces. The fifth peak extension force may not be more than 200%, or more than 150%, or more than 100% higher than one or both of the fourth and sixth transverse peak extension forces.

At the same time, it may be desirable to have a level of contraction in the transverse direction in the fifth zone 64 which does not vary more than 250%, or not more than 200%, or not more than 150% from the level of contraction in the transverse direction in the fourth and sixth zone 63 and 65.

This can be achieved by attaching the elastic strands of the fifth plurality of elastic strands to one or both of the third and fourth belt layer substantially along the complete length of the elastic strands, while attaching the elastic strands of the fourth and sixth plurality of elastic strands to one or both of the third and fourth belt layer (only) at or adjacent to the transversally opposing ends, or while attaching the elastic strands of the fourth and sixth plurality of elastic strands to one or both of the third and fourth belt layer (only) at or adjacent to the transversally opposing ends and in intervals of at least 10%, or at least 20% of the complete transverse extension of the elastic strands (measured when the elastic strands are in their relaxed, contracted state).

For further enhanced fit, the boundary between the fifth zone 64 and the sixth zone 65 may be provided at a distance of about 55% to 70%, or about 55% to 65% from the transverse centerline 110 of the absorbent article 100, wherein 100% is the entire front region extending from the transverse centerline 110 to the front waist edge 31. This can further help to position the fifth zone 64 in the low motion area of the wearer.

The boundary between the second zone 44 and the third zone 45 may be provided at a higher distance from the transverse centerline 110 than the distance between the transverse centerline 110 to the boundary between the fifth zone 64 to the sixth zone 65. The boundary between second zone 44 and the third zone 45 may be provided at a distance of about 60% to 80% from the transverse centerline 110 of the absorbent article 20, wherein 100% is the entire rear region extending from the transverse centerline 110 to the rear waist edge 32.

The transverse centerline 110 notionally divides the absorbent article 20 into a front region and a back region of equal length, i.e. equal longitudinal dimension. Hence, the distance from the transverse centerline 110 to the front waist edge 31 is the same as the distance from the transverse centerline 110 to the rear waist edge 32.

The first and second belt 40 and 60 may be discontinuous with one another in the crotch region 37. Thus, neither the first nor the second belt may cover the entirety of the body-facing surface and neither the first nor the second belt may cover the entirety of the garment-facing surface of the absorbent article 20.

Fastening System

The absorbent article 20 may also include a fastening system 140. When fastened, the fastening system 140 interconnects the front waist region 36 and the rear waist region 38 resulting in a waist circumference that provides a waist opening encircling the wearer during wear of the absorbent article 20. This may be accomplished by the first belt in the back waist region interconnecting with the center chassis in the front waist region (if the absorbent article does not comprise a second belt), or by the first belt interconnecting with the second belt in the front waist region. The fastening system 140 may be provided in an absorbent article which is a diaper with no permanent first and second side seam 57 and 58. Alternatively, the fastening system 140 may be provided in addition to first and second permanent side seams 57 and 58 in an absorbent article which is a pant, to facilitate further adjustment of the waist opening and/or to enable refastening the pant if one or both of the side seams have been torn open, e.g. when the pant is inspected for potential soiling.

The fastening system 140 may comprises a fastener such as hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 140 may also include primary and secondary fastening systems, as disclosed in U.S. Pat. No. 4,699,622. The fastening system 140 may be constructed to reduce shifting of overlapped portions or to improve fit as disclosed in U.S. Pat. Nos. 5,242,436; 5,499,978; 5,507,736; and 5,591,152. The fastening tabs may be attached to the first and second longitudinal belt side edges of the first belt. They may be configured to extend transversally outward beyond the first and second longitudinal belt side edges. The engaging material of the fastening tabs (e.g. hooks, adhesive etc.) may be provided on the portion of the fastening tab which extends transversally outward beyond the first and second longitudinal belt side edges. The fastening tabs may be folded prior to use of the absorbent article to keep the engaging material from engaging with an unintended portion of the absorbent article (e.g. during manufacturing of the absorbent article, or when taking the absorbent article out of a package prior to application on a wearer). When folded, the engaging material may contact a non-engagement surface comprised by the first belt adjacent to its first and second longitudinal belt side edges, such as a film, a polymer layer, or a non-tacky adhesive layer. When taken out of the package, the fastener tabs may be unfolded and engaged with a landing zone, such as a patch of loop material (often on the front waist region of the center chassis or on the second belt).

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 100 mm, less than about 95 mm, less than about 90 mm, less than about 85 mm, less than about 85 mm, but greater than about 75 mm, less than about 80 mm, less than about 78 mm, less than about 76 mm, or less than about 74 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 95 mm, from about 72 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 10:
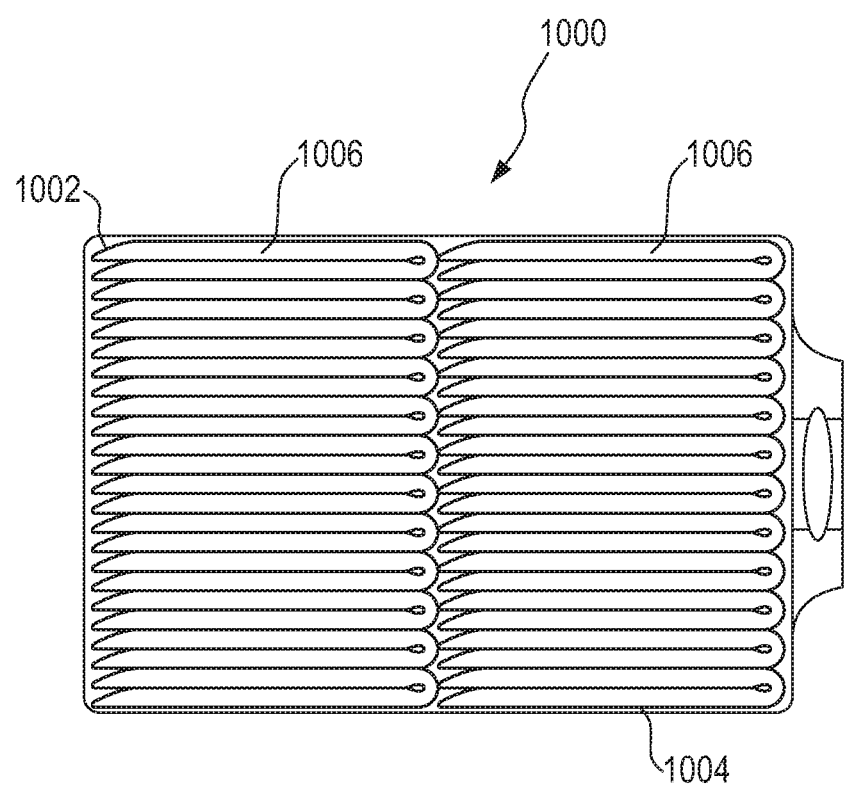
FIG. 10 illustrates an example package of a plurality of the absorbent articles (taped or pant) of the present disclosure.

FIG. 10 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Test Methods

Transverse Peak Extension Force

Test Equipment/Environment

A suitable tensile tester such as an MTS Alliance with MTS Testworks version 4.0 or equivalent instrument is used. The tester is equipped with flat clamps that are capable of holding at least the entire width of the sample should be used. The instrument is calibrated according to the manufacturer's specification. Testing is performed at 23° C.±2° C. and 50%±2% relative humidity.

Sample Preparation

If the absorbent article is a pant with permanent side seams between first and second belt, the side seams of the article are broken to separate the belts. The respective zones (as described in the Detailed Description of the Invention) are cut out from the respective belt (including center chassis components, if overlapping with the respective belt zone) to be measured. Each separated zone of the respective belt will be referred to as a "test sample" herein. All material layers, including the center chassis components if present, should be kept with the test sample. All cut lines are straight, parallel to the transverse direction of the absorbent article. Each test sample needs to have at least one elastomeric material. The widths (a dimension in the longitudinal direction of the absorbent article) of the respective zones are measured.

The length of the test sample is determined. The length corresponds to the direction which corresponds to the transverse direction of the absorbent article and measures a distance from one end to the other end of a test sample in a fully stretched condition. The fully stretched condition is the condition where the test sample is stretched by the force of 0.1 N/mm multiplied by the width of the test sample. If one or both ends of a test sample are not parallel to the longitudinal direction, the shortest length within the test sample is considered as the length of the test sample.

An adjusted test sample length is defined as the length of a test sample minus the combined length of any material in the upper and lower clamps. Thus, if a test sample is mounted in the clamp so that 10 mm at each end is held in the clamps, then the adjusted belt length is the measured belt length minus 20 mm.

The test samples are kept unstretched at least for 10 min before the test.

Test

For each test sample, the initial gauge length of the tensile tester is set to allow the test sample to be mounted in a relaxed state. The load cell is zeroed to offset the sample weight.

The test sample is stretched in the transverse direction of the absorbent article at a rate of 254 mm/min, and a load (N) is measured within 5 sec after the test sample reaches at 65% of the adjusted test sample length. The transverse peak extension force is calculated for each of the force zones according to an equation:

A transverse peak extension force (N/mm) of a test sample=Measured value (N)/width of the force zone (mm)

Level of Contraction a) Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23° C.±2° C. and 50%±2% relative humidity.

Figure 11:
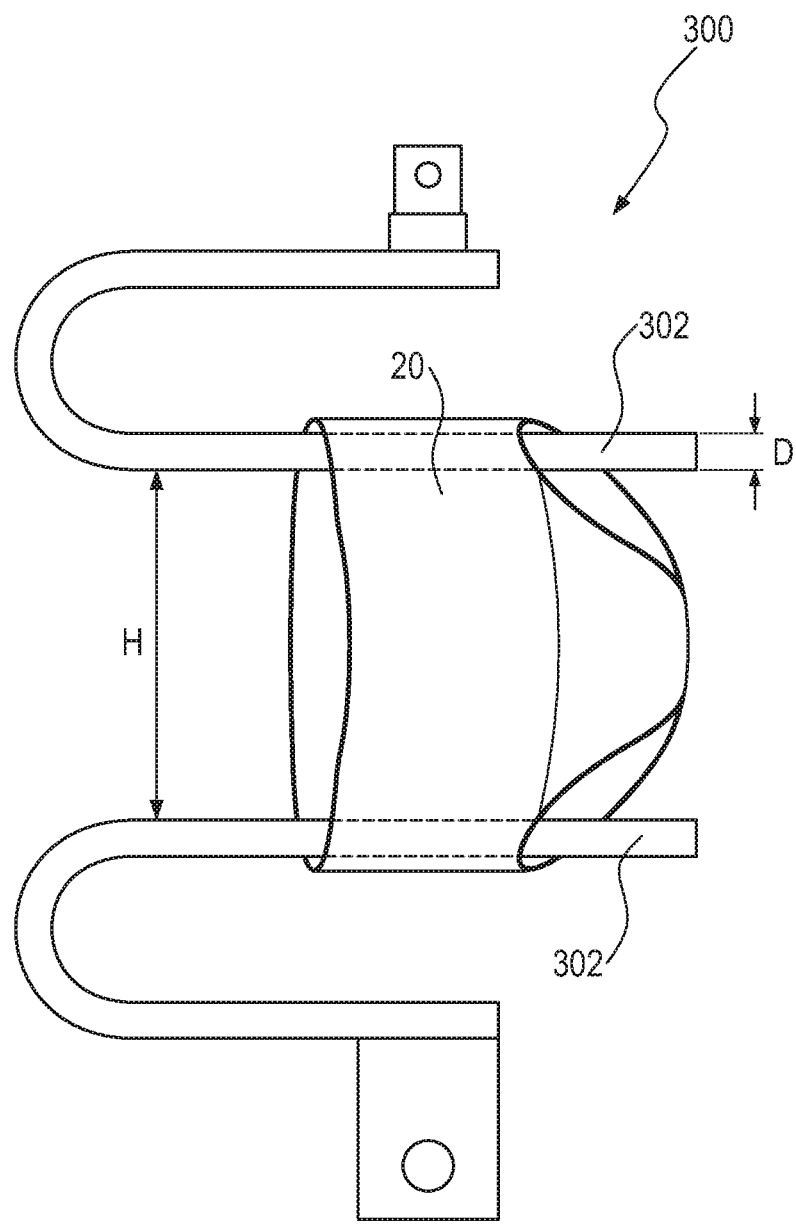
FIG. 11 is a schematic view of an example of a hanger-type sample holding fixture according to "Whole Article Force Measurement".

The tensile tester is fitted with hanger-type sample holding fixtures 300 as shown in FIG. 11. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

Gauge Circumference=2×(H+D+πD/2)

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.61 N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and crosshead is lowered to enable the lower bar 302 to be inserted through the waist opening and other leg opening without stretching the article. The article is adjusted so that the longitudinal centerline 100 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and crosshead moves up at 254 mm/min until a force of 19.6N is attained, then the crosshead immediately returns to the initial gauge circumference at the same speed. The maximum circumference at 19.6N and force at 70% stretch circumference during the extension segment of the test are recorded.

Circumference (mm)=2×(H+D+πD/2)

The maximum circumference at 19.6N is defined as the Full Stretch Circumference (mm). The 70% stretch circumference is defined as the full stretch circumference×0.7. The Waist Circumference Force is defined as the force at 70% stretch circumference during the load (extension) segment of the test.

Five samples are analyzed and their average Initial Gauge Circumference, average Full Stretch Circumference and average Waist Circumference Force are calculated and reported to the nearest 1 mm, 1 mm and 0.01 N, respectively.

b) Measurement of Zone Transverse Dimension

After the sample has been subjected to the Whole Article Force Measurement Test, the sample is prepared and treated as follows:

Test Equipment/Environment

A suitable tensile tester such as an MTS Alliance with MTS Testworks version 4.0 or equivalent instrument is used. The tester is equipped with flat clamps that are capable of holding at least the entire width of the sample should be used. The instrument is calibrated according to the manufacturer's specification. Testing is performed at 23° C.±2° C. and 50%±2% relative humidity.

Sample Preparation

If the absorbent article is a pant with permanent side seams between first and second belt, the side seams of the article are broken to separate the belts. The respective zones (as described in the Detailed Description of the Invention) are cut out from the respective belt (including center chassis components, if overlapping with the respective belt zone) to be measured. All material layers, including the center chassis components if present, should be kept with the test sample (i.e. with the cut out zone). All cut lines are straight, parallel to the transverse direction of the absorbent article. Each test sample needs to have at least one elastomeric material. The widths (a dimension in the longitudinal direction of the absorbent article) of the respective zones are measured.

The length of the test sample is determined. The length measures in the transverse direction of the absorbent article a distance from one end to the other end of a test sample in a fully stretched condition. The fully stretched condition is the condition where the test sample is stretched by the force of 0.1 N/mm multiplied by the width of the test sample. If one or both ends of a test sample are not parallel to the longitudinal direction, the shortest length within the test sample is considered as the length of the test sample.

An adjusted test sample length is defined as the length of a test sample minus the combined length of any material in the upper and lower clamps. Thus, if a test sample is mounted in the clamp so that 10 mm at each end is held in the clamps, then the adjusted belt length is the measured belt length minus 20 mm.

For each test sample, the initial gauge length of the tensile tester is set to allow the test sample to be mounted in a relaxed state. The load cell is zeroed to offset the sample weight.

The test sample is stretched in the transverse direction of the absorbent article by applying a force of 0.5 N is applied to the test sample in the direction which corresponds to the transverse direction of the absorbent article. The length of the test sample (corresponding to the transverse dimension of the respective zone in the absorbent article) is measured, taking into account the 20 mm comprised between the clamps of the tensile tester.

The level of contraction is then calculated as follows:

(Length of the test sample of the respective zone @0.5 N×100)/(½ of maximum circumference at 19.6N*))

*) maximum circumference taken from Whole Article Force Measurement

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 10). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

All documents cited in the Detailed Description of the Invention are, in relevant part, incorporated herein by reference; the citation of any document is not to be construed as an admission that it is prior art with respect to the present disclosure. To the extent that any definition or meaning of a term in this written document conflicts with any definition or meaning of the term in a document incorporated by reference, the definition or meaning assigned to the term in this document shall govern.

While particular embodiments of the present disclosure have been illustrated and described, it would be obvious to those skilled in the art that various other changes and modifications can be made without departing from the spirit and scope of the disclosure. It should be apparent that combinations of such embodiments and features are possible and can result in executions within the scope of this disclosure. It is therefore intended to cover in the appended claims all such changes and modifications that are within the scope of this disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. An absorbent article comprising:
   a longitudinal and transverse dimension;
   a front waist region comprising a front waist edge;
   a rear waist region comprising a rear waist edge;
   a crotch region extending between the front and rear waist region;
   a center chassis comprising a first transverse chassis end edge, a second transverse chassis end edge, a first longitudinal chassis side edge and a second longitudinal chassis side edge, a liquid permeable topsheet, a liquid impermeable backsheet, and an absorbent core disposed between the topsheet and the backsheet;
   a first belt is provided in the rear waist region and comprises a first belt layer disposed on an interior surface of the first belt, a second belt layer disposed on an exterior surface of the first belt and elastic strands extending substantially along the transverse direction disposed between the first belt layer and the second belt layer;
   wherein the first belt comprises a first zone, a second zone and a third zone, the first zone being provided adjacent to and including the rear waist edge, and the second zone being provided between the first and third zone in a longitudinal direction of the absorbent article;
   wherein the elastic strands of the first zone comprise a first plurality of elastic strands that are attached to one or both of the first belt layer and the second belt layer at or adjacent the transversally opposing ends of the first plurality of elastic strands;

wherein the first belt layer and second belt layer are joined to each other between pairs of elastic strands of the first plurality of elastic strands in the first zone;

wherein the elastic strands of the second zone comprise a second plurality of elastic strands that are attached to one or both of the first belt layer and second belt layer along substantially the complete length of the elastic strands;

wherein the elastic strands of the third zone comprise a third plurality of elastic strands that are attached to one or both of the first belt layer and the second belt layer at or adjacent the transversally opposing ends of the third plurality of elastic strands; and wherein the first belt layer and second belt layer are joined to each other between pairs of elastic strands of the third plurality of elastic strands in the third zone.

2. The absorbent article of claim 1 further comprising a second belt, wherein the second belt is provided in the front waist region, the second belt comprising:

a third belt layer disposed on an interior surface of the second belt, a fourth belt layer disposed on an exterior surface of the second belt and elastic strands extending substantially along the transverse direction disposed between the third belt layer and the fourth belt layer;

a fourth zone, a fifth zone and a sixth zone; the fourth zone being provided adjacent to and including the front waist edge, and the fifth zone being provided between the fourth and sixth zone in a longitudinal direction of the absorbent article;

wherein the elastic strands of the fourth zone comprise a fourth plurality of elastic strands that are attached to one or both of the third belt layer and the fourth belt layer at or adjacent the transversally opposing ends of the fourth plurality of elastic strands;

wherein the third belt layer and fourth belt layer are joined to each other between pairs of elastic strands of the fourth plurality of elastic strands in the fourth zone;

wherein the elastic strands of the fifth zone comprise a fifth plurality of elastic strands that are attached to one or both of the third belt layer and the fourth belt layer along substantially the complete length of the elastic strands;

wherein the elastic strands of the sixth zone comprise a sixth plurality of elastic strands that are attached to one or both of the third belt layer and the fourth belt layer at or adjacent the transversally opposing ends of the elastic strands; and wherein the third belt layer and the fourth belt layer are joined to each other between pairs of elastic strands of the sixth plurality of elastic strands in the sixth zone.

3. The absorbent article of claim 2, wherein the absorbent article is a pant and wherein the first belt comprises first and second longitudinal belt side edges and the second belt comprises third and fourth longitudinal belt side edges, wherein the first longitudinal belt side edge of the first belt is joined to the third longitudinal belt side edge of the second belt to form a first side seam, and the second longitudinal belt side edge of the first belt is joined to the fourth longitudinal belt side edge of the second belt to form a second side seam.

4. The absorbent article of claim 2, wherein, when the first and second belt are put in an overlapping configuration such that the front and rear waist edges coincide with each other, the second zone and the fifth zone partly overlap.

5. The absorbent article of any of claim 2, wherein the second zone is disposed at a first distance L1 longitudinally offset from the rear waist edge of the absorbent article, the fifth zone is disposed at a second distance (L2) longitudinally offset from the front waist edge of the absorbent article and the first distance (L1) is not equal to the second distance (L2).

6. The absorbent article of claim 5, wherein the third zone is disposed at a third distance (L3) longitudinally offset from the rear waist edge of the absorbent article, the sixth zone is disposed at a fourth distance (L4) longitudinally offset from the front waist edge of the absorbent article and the third distance (L3) is not equal to the fourth distance (L4).

7. The absorbent article of claim 2, wherein the second belt has a third transverse belt end region adjacent to the third longitudinal belt side edge, a fourth transverse belt end region adjacent to the fourth longitudinal belt side edge, and a second central belt region between the third and fourth transverse belt end regions, wherein the elastic strands of the sixth plurality of elastic strands and at least some of the fifth plurality of elastic strands are severed to form a third segment disposed in the third transverse belt end region and a fourth segment disposed in the fourth transverse belt end region, wherein the second central belt region is free of the severed elastic strands from the sixth plurality of elastic strands and is free of the severed elastic strands of the fifth plurality of elastic strands.

8. The absorbent article of claim 2, wherein, in the first belt, the first belt layer and second belt layer are adhesively joined to each other between pairs of elastic strands of the first and third plurality of elastic strands in the first and third zone, and wherein, in the second belt, the third belt layer and fourth belt layer are adhesively joined to each other between pairs of elastic strands of the fourth and sixth plurality of elastic strands in the fourth and sixth zone.

9. The absorbent article of any of claim 2, wherein the elastic strands of the second plurality of elastic strands are continuously attached to one or both of the first and second belt layer along the complete length of the elastic strands by adhesive, and the elastic strands of the fifth plurality of elastic strands are continuously glued to one or both of the third and fourth belt layer along the complete length of the elastic strands by adhesive.

10. The absorbent article of claim 1, wherein the first belt has a first transverse belt end region adjacent to the first longitudinal belt side edge, a second transverse belt end region adjacent to the second longitudinal belt side edge, and a first central belt region between the first and second transverse belt end regions, wherein the elastic strands of the third plurality of elastic strands and at least some of the second plurality of elastic strands are severed to form discontinuous elastic strands with a first segment disposed in the first transverse belt end region and a second segment disposed in the second transverse belt end region, wherein the first central belt region is free of the severed elastic strands from the third plurality of elastic strands and is free of the severed elastic strands of the second plurality of elastic strands.

11. The absorbent article of claim 1, wherein the first zone has a first transverse peak extension force, the second zone has a second transverse peak extension force and the third zone has a third transverse peak extension force, wherein the transverse peak extension force of the second zone is at least 25% higher than the transverse peak extension force of the first and third zone and wherein the level of contraction in the transverse direction in the second zone does not vary more than 250% from the level of contraction in the first and third zone.

12. The absorbent article of claim 11, wherein the fourth zone has a fourth transverse peak extension force, the fifth zone has a fifth transverse peak extension force and the sixth zone has a sixth transverse peak extension force, wherein the transverse peak extension force of the fifth zone is at least 25% higher than the transverse peak extension force of the fourth and sixth zone and wherein the level of contraction in the transverse direction in the fifth zone does not vary more than 250% from the level of contraction in the fourth and sixth zone.

13. The absorbent article of claim 1, wherein the first transverse end edge of the center chassis coincides with the rear waist edge of the absorbent article and/or the second transverse end edge of the center chassis coincides with the first waist edge of the absorbent article.

14. The absorbent article of claim 1, wherein some of the elastic strands of the first belt and/or the optional second belt are arranged in one or more sets as one or more concentrated arrays, wherein each concentrated array consists of two to four elastic strands, and wherein the elastic strands in the concentrated array are longitudinally spaced apart from each other by a gap of from two to four millimeter and wherein the elastic strands in the first and/or in the optional second belt outside the concentrated arrays are longitudinally spaced apart from the concentrated arrays and from each other by a gap of from 5 to 10 millimeter.

15. The absorbent article of claim 1, wherein the elastic strands of the second plurality of elastic strands differ from the elastic strands of the first and/or third plurality of elastics in one or more properties selected from the group consisting of: strain of the elastic strands, distance between neighboring elastic strands, number of elastic strands forming the plurality of elastic strands and denier of the elastic strands.

* * * * *